(12) United States Patent
Bucher et al.

(10) Patent No.: US 12,144,299 B2
(45) Date of Patent: Nov. 19, 2024

(54) MOBILISATION OF TRANSPOSABLE ELEMENTS TO ENHANCE GENETIC AND EPIGENETIC VARIABILITY IN A POPULATION

(71) Applicant: UNIVERSITAT BASEL, Basel (CH)

(72) Inventors: Etienne Bucher, Beaucouze (CH); Michael Thieme, Zollikon (CH)

(73) Assignee: UNIVERSITAT BASEL, Basel (CH)

( * ) Notice: Subject to any disclaimer, the term of this patent is extended or adjusted under 35 U.S.C. 154(b) by 243 days.

(21) Appl. No.: 15/780,636

(22) PCT Filed: Nov. 30, 2016

(86) PCT No.: PCT/EP2016/079276
§ 371 (c)(1),
(2) Date: Jun. 1, 2018

(87) PCT Pub. No.: WO2017/093317
PCT Pub. Date: Jun. 8, 2017

(65) Prior Publication Data
US 2018/0352764 A1 Dec. 13, 2018

(30) Foreign Application Priority Data
Dec. 2, 2015 (EP) .................... 15197663

(51) Int. Cl.
*A01H 3/04* (2006.01)
*A01H 1/06* (2006.01)
*C12N 15/01* (2006.01)
*C12N 15/82* (2006.01)

(52) U.S. Cl.
CPC ............... *A01H 1/06* (2013.01); *A01H 3/04* (2013.01); *C12N 15/01* (2013.01); *C12N 15/8201* (2013.01); *C12N 15/8216* (2013.01)

(58) Field of Classification Search
None
See application file for complete search history.

(56) References Cited

FOREIGN PATENT DOCUMENTS

| CN | 1748479 | 3/2006 |
|---|---|---|
| JP | 2003-093074 | 4/2003 |
| JP | 2008187967 | 8/2008 |

OTHER PUBLICATIONS

Bilichak et al (Plant Biotechnology Journal, 2014, 12: 590-600).*
Shin et al (PLOS Genetics, 2014, 10(9): e1004612).*
Zheng et al (Genes Dev, 2009, 23(24): 2850-2860).*
Ito et al (Nature, 2011, 472: 115-119).*
Baubec et al (EMBO Reports, 2014, 15(4):446-452).*
Bennetzen (Plant Molecular Biology, 2000, 42:251-269).*
Gao et al (Nature, 2010, 465: 106-109).*
Salazar et al, 2007, Plant Cell Rep 26:1861-1868.*
Melayah et al, 2005, Cytogenet Genome Res, 110:229-241.*
Ito et al, 2011, Nature, 472:115-120.*
Dhaval Varshney et al: "Sine transcription by RNA polymerase III is suppressed by histone methylation but not by DNA methylation", Nature Communication, vol. 6, Mar. 23, 2015, p. 6569.
Tuncay Baubec et al: "Effective homogeneous and transient interference with cytosine methylation in plant genomic DNA by zebularine", The Plant Journal, vol. 57, No. 3, Feb. 1, 2009, pp. 542-554.
Vladimir V. Cavrak et al: "How a Retrotransposon Exploits the Plant's Heat Stress Response for Its Activation", PLOS Genetics, vol. 10, No. 1, Jan. 30, 2014, p. e1004115.
W. Matsunaga et al: "The effects of heat induction and siRNA biogenesis pathway on the transgenerational transposition of ONSEN, a copia-like retrotransposon in *Arabidopsis thaliana*", Plant and Cell Physiology, vol. 53, No. 5, Dec. 14, 2011, pp. 824-833.
Marjori A. Matzke et al: "RNA-directed DNA methylation: an epigenetic pathway of increasing complexity", Nature Reviews Genetics, vol. 15, No. 6, May 8, 2014, pp. 394-408.
Wataru Matsunaga et al: "Role of RNA polymerase IV in plant small RNA metabolism", Frontiers in Plant Science, vol. 104, No. e129, Feb. 9, 2015, p. 4536.
Bucher Etienne et al: "Epigenetic control of transposon transcription and mobility in Arabidopsis", Current Opinion in Plant Biology, vol. 15, No. 5, 2012, pp. 503-510.
S. Vispe et al: "Triptolide is an inhibitor of RNA polymerase I and II-dependent transcription leading predominantly to down-regulation of short-lived mRNA", Molecular Cancer Therapeutics, vol. 8, No. 10, Oct. 1, 2009, pp. 2780-2790.
H. Saze et al: "DNA Methylation in Plants: Relationship to Small RNAs and Histone Modifications, and Functions in Transposon Inactivation", Plant and Cell Physiology, vol. 53, No. 5, Feb. 1, 2012, pp. 766-784.
Varshney et al. "SINE transcription by RNA polymerase III is suppressed by histone methylation but not by DNA methylation." Nat Commun 6, 6569 (2015). https://doi.org/10.1038/ncomms7569.
Baubec et al, "Effective, homogeneous and transient interference with cytosine methylation in plant genomic DNA by zebularine", The Plant Journal, GB, (Feb. 1, 2009), vol. 57, No. 3, doi:10.1111/j.1365-313X.2008.03699.x, ISSN 0960-7412, pp. 542-554, XP055271538 [I] 8, 12, 16 * Abstract; pp. 543,546-548, 550; figure 6.

(Continued)

*Primary Examiner* — Jason Deveau Rosen
(74) *Attorney, Agent, or Firm* — JMB Davis Ben-David

(57) ABSTRACT

A method for the mobilization of a transposable element is provided. The method comprises the steps of a) providing an inhibitor of DNA methylation, and/or an inhibitor of transcription, and b) contacting the inhibitor(s) with a cell comprising inactivated transposable elements, yielding a cell with mobilized transposable elements. In a second aspect of the invention a method for increasing the genetic and/or epigenetic variation in a plurality of eukaryotic organisms is provided. The method comprises the steps of i. providing an inhibitor of DNA methylation and/or an inhibitor of transcription, ii. contacting the organism with the inhibitor(s) and iii. propagating the organism.

4 Claims, 21 Drawing Sheets

Figure 1:
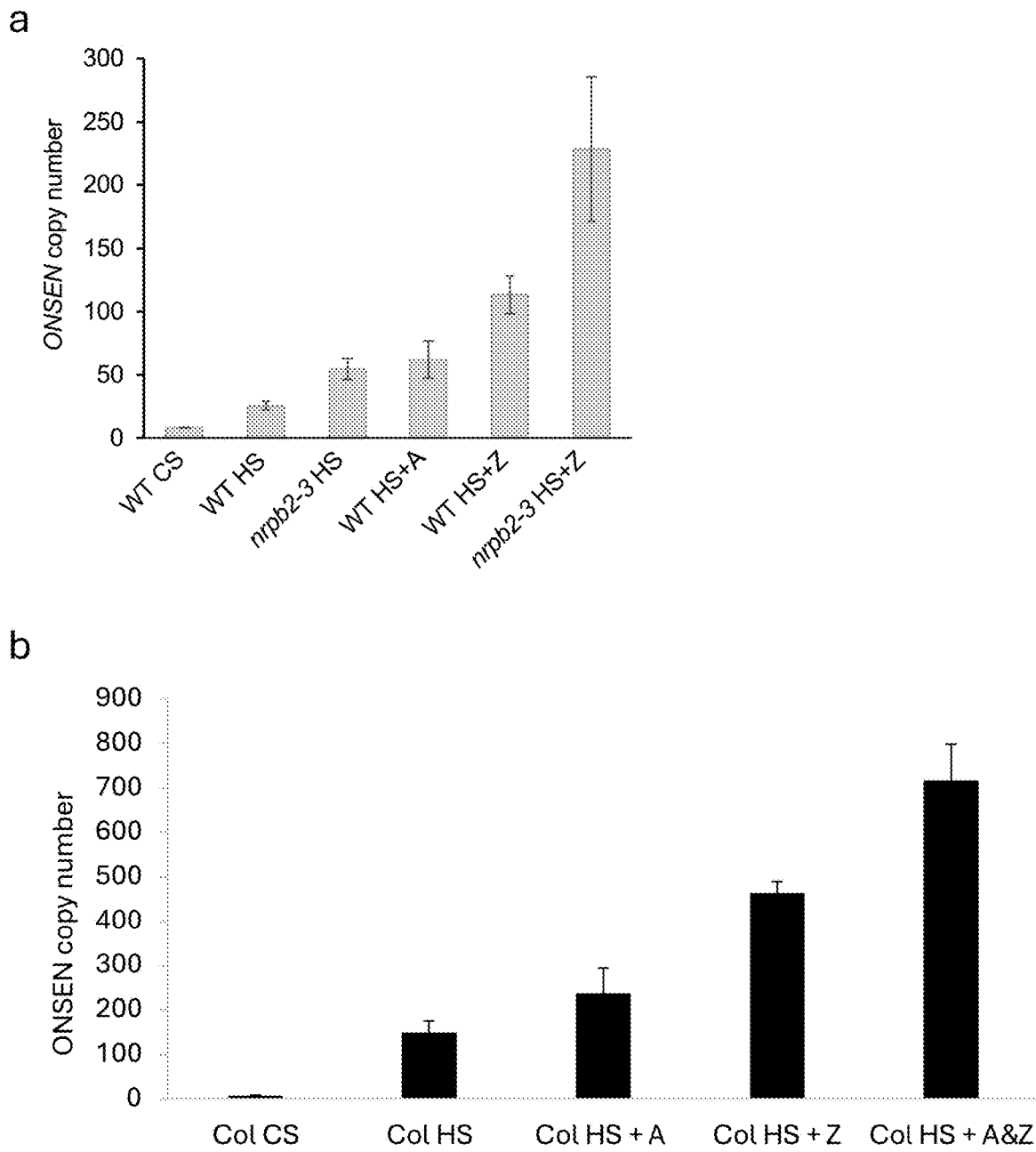

Specification includes a Sequence Listing.

(56) References Cited

OTHER PUBLICATIONS

Cavrak et al. (2014) How a Retrotransposon Exploits the Plant's Heat Stress Response for Its Activation. PLOS Genetics 10(1): e1004115. https://doi.org/10.1371/journal.pgen.1004115.
Matsunaga et al, "The effects of heat induction and the siRNA biogenesis pathway on the transgenerational transposition of ONSEN, a copia-like retrotransposon in *Arabidopsis thaliana*", Plant and Cell Physiology, Uk, (Dec. 14, 2011), vol. 53, No. 5, doi: 10.1093/pcp/pcr179, ISSN 0032-0781, pp. 824-833, XP055271560 [A] 1-19 * the whole document * . DOI: http://dx.doi.org/10.1093/pcp/pcr179.
Matzke et al, "RNA-directed DNA methylation: an epigenetic pathway of increasing complexity", Nature Reviews Genetics, GB, (May 8, 2014), vol. 15, No. 6, doi:10.1038/nrg3683, ISSN 1471-0056, pp. 394-408, XP055271562 [A] 1-19 * the whole document * DOI: http://dx.doi.org/10.1038/nrg3683.
Matsunaga et al, "Role of RNA polymerase IV in plant small RNA metabolism.", Frontiers in Plant Science, (Feb. 9, 2015), vol. 104, No. e129, doi:10.1073/pnas.0611456104, p. 4536, XP055271567 [A] 1-19 * the whole document.
Etienne et al, "Epigenetic control of transposon transcription and mobility in Arabidopsis", Current Opinion in Plant Biology, (2012), vol. 15, No. 5, doi:10.1016/J.PBI.2012.08.006, ISSN 1369-5266, pp. 503-510, XP028958933 [A] 1-19 * the whole document *. DOI: http://dx.doi.org/10.1016/j.pbi.2012.08.006.
Vispe et al., "Triptolide is an inhibitor of RNA polymerase I and II-dependent transcription leading predominantly to down-regulation of short-lived mRNA", Molecular Cancer Therapeutics, US, (Oct. 1, 2009), vol. 8, No. 10, doi:10.1158/1535-7163.MCT-09-0549, ISSN 1535-7163, pp. 2780-2790, XP055272275 [A] 1-19 * the whole document * DOI: http://dx.doi.org/10.1158/1535-7163.MCT-09-0549.
Saze et al, "DNA Methylation in Plants: Relationship to Small RNAs and Histone Modifications, and Functions in Transposon Inactivation", Plant and Cell Physiology, UK, (Feb. 1, 2012), vol. 53, No. 5, doi: 10.1093/pcp/pcs008, ISSN 0032-0781, pp. 766-784, XP055272283 [A] 1-19 * abstract; pp. 774, 776, 777 * . DOI: http://dx.doi.org/10.1093/pcp/pcs008.
Thieme et al. "Inhibition of RNA polymerase II allows controlled mobilisation of retrotransposons for plant breeding." Genome Biol 18, 134 (2017). https://doi.org/10.1186/s13059-017-1265-4.
Hudson et al., "Changes in global gene expression in responseto chemical and genetic perturbation of chromatin structure.," PLoS ONE, 2011, vol. 6, No. 6, e20587.
Onodera et al. "Plant Nuclear RNA Polymerase IV Mediates siRNA and DNA Methylation-Dependent Heterochromatin Formation" 2005, and vol. 120 and p. 613-622.
Mizrokhi et al., "Jockey, a mobile Drosophila element similar to mammalian LINEs, and is transcribed from the internal promoter by RNA polymerase II," Cell, 1988, and vol. 54, No. 5 and p. 685-691.
Tan et al. "Proteomic insights into seed germination in response to environmental factors," Proteomics, 2013, and vol. 13 and p. 1850-1870.
Shin et al "*Arabidopsis* RRP6L1 and RRP6L2 Function in Flowering Locus C Silencing via Regulation of Antisense RNA Synthesis." PLOS Genetics 10(9): e1004612. https://doi.org/10.1371/journal.pgen.1004612.
Zheng et al., "Intergenic transcription by RNA Polymerase II coordinates PolIV and PolV in siRNA-directed transcriptional gene silencing in *Arabidopsis*," Genes & Development, 23, 2850-2860.
Ito et al., "An siRNA pathway prevents transgene rational retrotransposition in plants subjectefd to stress," Nature, 2011, 472, 115-119.
Zi-Cheng et al "Plant Retrotransposons and Their Molecular Markers[J]". Chinese Bulletin of Botany, 2003, 20(03):287-294.
Huang et al "Studies on Polyploidization of chromosome set in Poaceae," p. 76, 2008, ISBN 978-7-5022-4262-6.
Thieme et al. "Experimentally heat-induced transposition increases drought tolerance in *Arabidopsis thaliana*" New Phytologist (2022) doi: 10.1111/nph.18322 (13 pages).

* cited by examiner

Fig. 1a, b

Fig. 3a, b
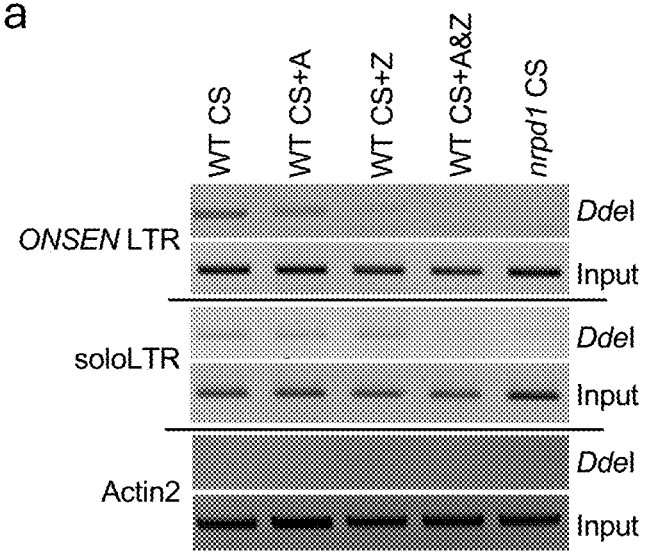
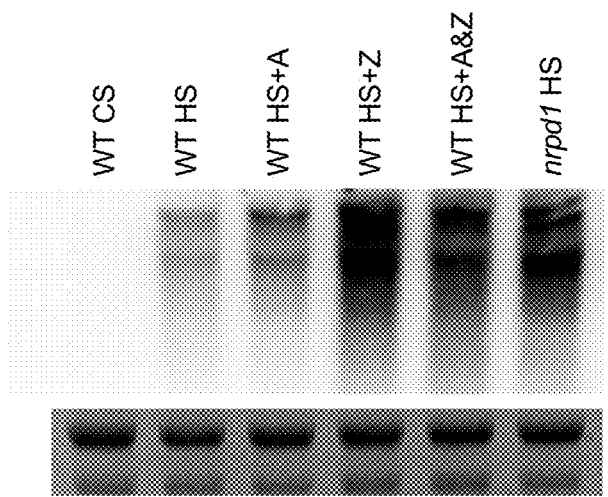

Fig. 4c,d
c
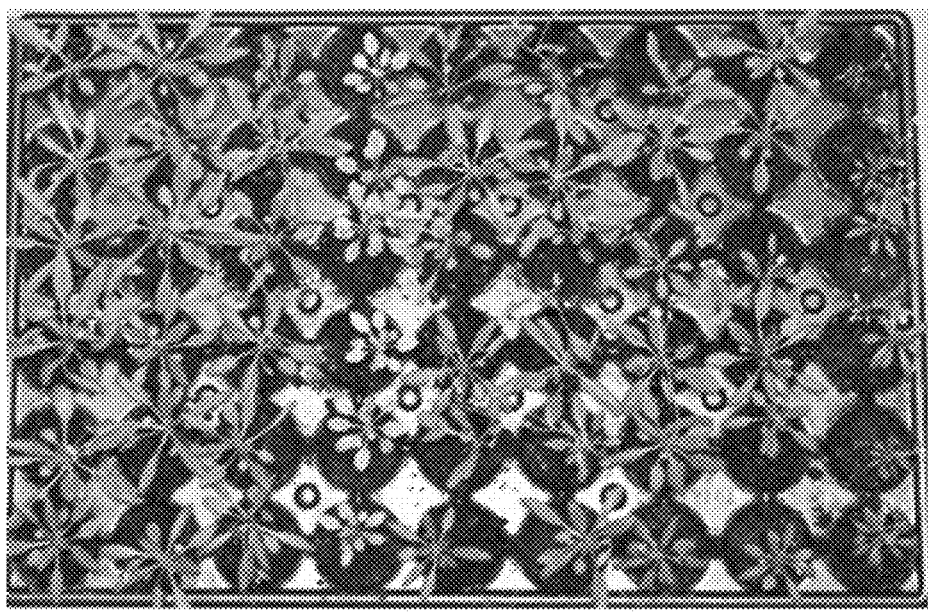
a   b   c   1   2   3   4   5   7
d
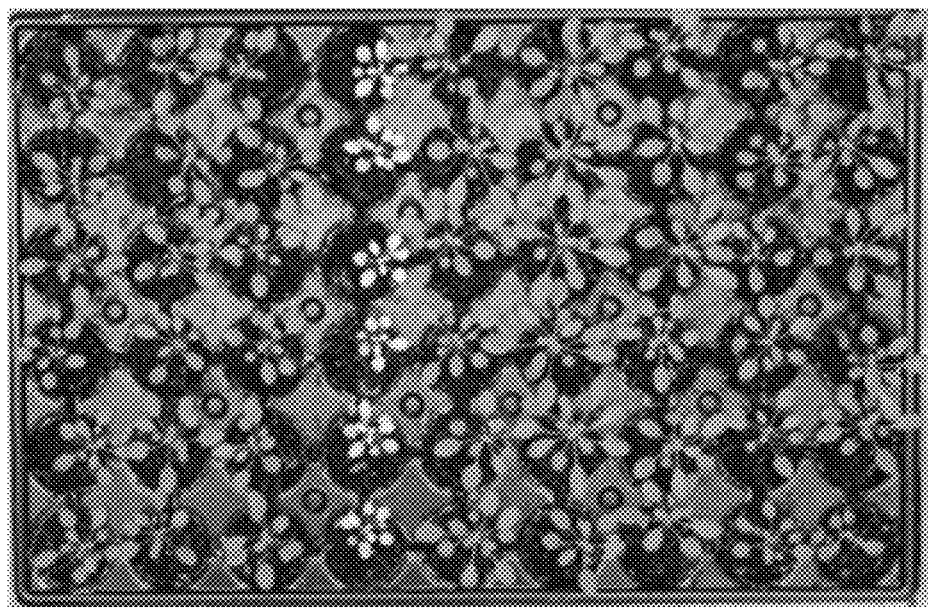

Fig. 7b-d
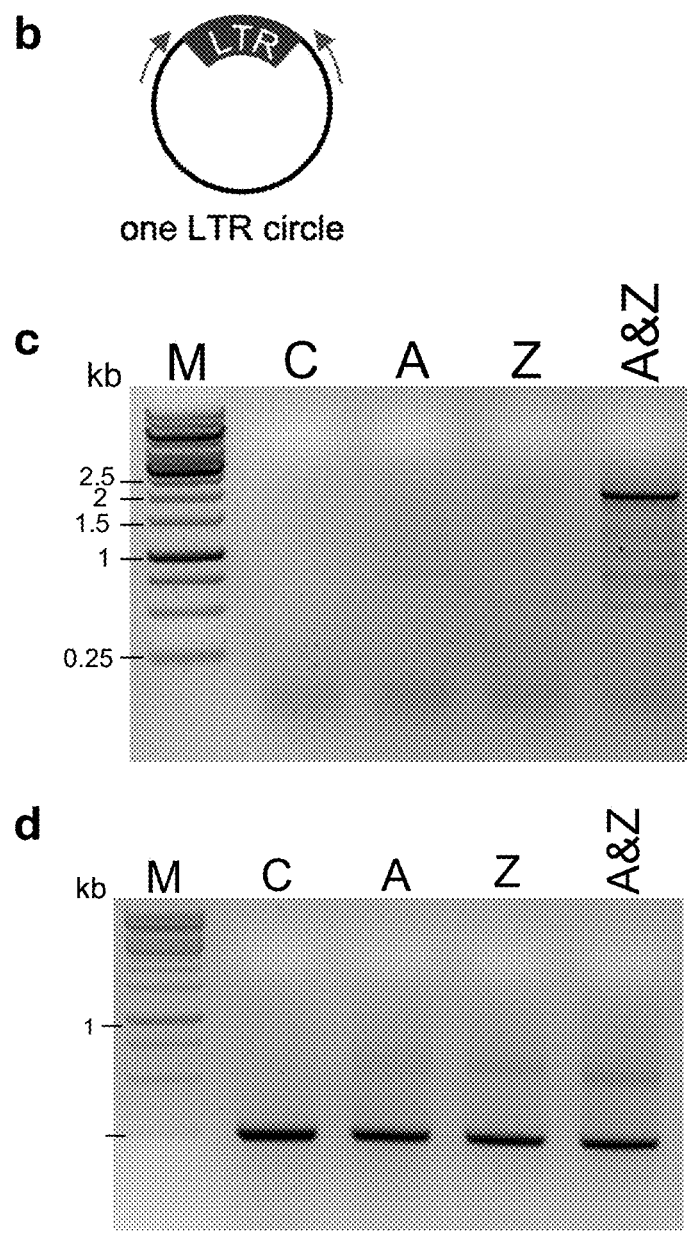

Figure 10:
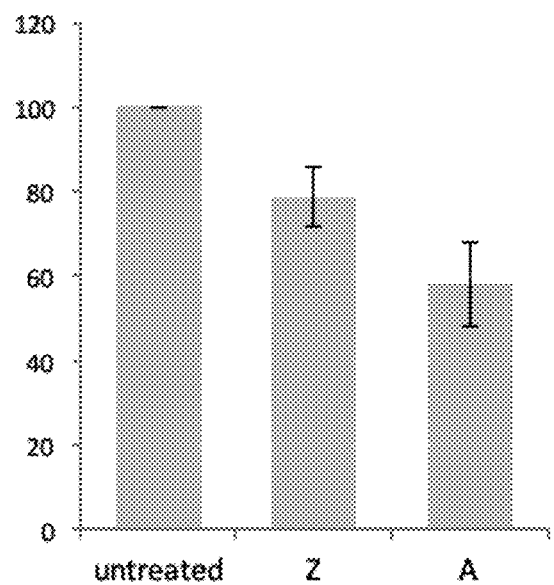

Fig. 10 a,b,c
a
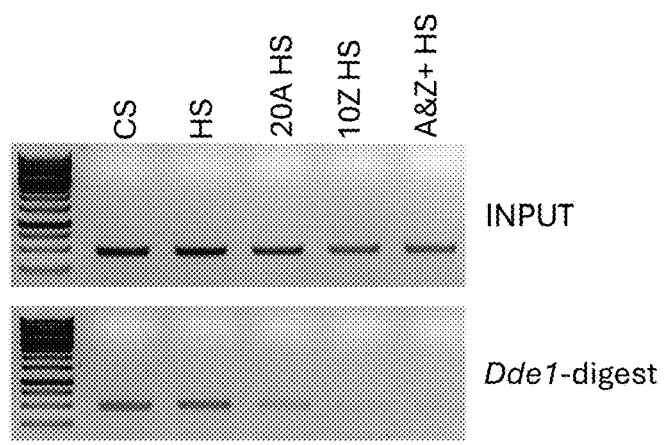
b
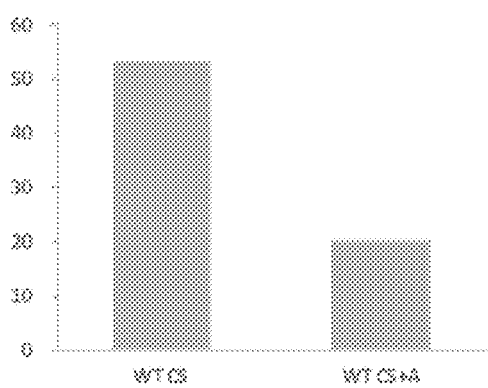
c
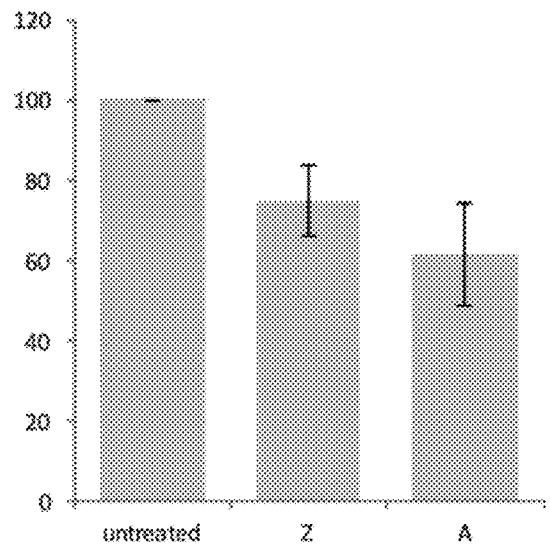

SEQUENCE LISTING

<160> NUMBER OF SEQ ID NOS: 37

<210> SEQ ID NO 1
<211> LENGTH: 20
<212> TYPE: DNA
<213> ORGANISM: Artificial Sequence
<220> FEATURE:
<223> OTHER INFORMATION: RT PCR primer for ONSEN from Arabidopsis
      thaliana

<400> SEQUENCE: 1
ccacaagagg aaccaacgaa                                              20

<210> SEQ ID NO 2
<211> LENGTH: 19
<212> TYPE: DNA
<213> ORGANISM: Artificial Sequence
<220> FEATURE:
<223> OTHER INFORMATION: RT PCR primer for ONSEN from Arabidopsis
      thaliana

<400> SEQUENCE: 2
ttcgatcatg gaagaccgg                                                19

<210> SEQ ID NO 3
<211> LENGTH: 25
<212> TYPE: DNA
<213> ORGANISM: Artificial Sequence
<220> FEATURE:
<223> OTHER INFORMATION: RT PCR probe for ONSEN from Arabidopsis
      thaliana
<220> FEATURE:
<221> NAME/KEY: misc_feature
<222> LOCATION: (1)..(1)
<223> OTHER INFORMATION: FAM dye at the 3' end
<220> FEATURE:
<221> NAME/KEY: misc_feature
<222> LOCATION: (25)..(25)
<223> OTHER INFORMATION: BHQ1 quencher at the 5' end

<400> SEQUENCE: 3
aagtcggcaa tagctttggc gaaga                                         25

<210> SEQ ID NO 4
<211> LENGTH: 20
<212> TYPE: DNA
<213> ORGANISM: Artificial Sequence
<220> FEATURE:
<223> OTHER INFORMATION: RT PCR primer for actin2 of Arabidopsis
      thaliana

<400> SEQUENCE: 4
tgccaatcta cgagggtttc                                               20

<210> SEQ ID NO 5
<211> LENGTH: 20
<212> TYPE: DNA
<213> ORGANISM: Artificial Sequence
<220> FEATURE:
<223> OTHER INFORMATION: RT PCR primer for actin2 of Arabidopsis
      thaliana

<400> SEQUENCE: 5
ttacaatttc ccgctctgct                                               20

<210> SEQ ID NO 6
<211> LENGTH: 22
<212> TYPE: DNA
<213> ORGANISM: Artificial Sequence
<220> FEATURE:
<223> OTHER INFORMATION: Actin2 probe for RT PCR
<220> FEATURE:
<221> NAME/KEY: misc_feature
<222> LOCATION: (1)..(1)
<223> OTHER INFORMATION: JOE dye at the 3' end
<220> FEATURE:
<221> NAME/KEY: misc_feature
<222> LOCATION: (22)..(2)
<223> OTHER INFORMATION: BHQ-1 quencher at the 5' end

<400> SEQUENCE: 6
tccgtcttga ccttgctgga cg                                            22

<210> SEQ ID NO 7
<211> LENGTH: 48
<212> TYPE: DNA
<213> ORGANISM: Artificial Sequence
<220> FEATURE:
<223> OTHER INFORMATION: GenWalkAdaptor1

```
<400> SEQUENCE: 7
gtaatacgac tcactatagg gcacgcgtgg tcgacggccc gggctggt         48

<210> SEQ ID NO 8
<211> LENGTH: 22
<212> TYPE: DNA
<213> ORGANISM: Artificial Sequence
<220> FEATURE:
<223> OTHER INFORMATION: PCR primer specific for GenWalkAdaptor

<400> SEQUENCE: 8
gtaatacgac tcactatagg gc                                     22

<210> SEQ ID NO 9
<211> LENGTH: 21
<212> TYPE: DNA
<213> ORGANISM: Artificial Sequence
<220> FEATURE:
<223> OTHER INFORMATION: PCR primer specific for ONSEN of Arabidopsis
      thaliana

<400> SEQUENCE: 9
aacacttaaa cactttctcc a                                      21

<210> SEQ ID NO 10
<211> LENGTH: 26
<212> TYPE: DNA
<213> ORGANISM: Artificial Sequence
<220> FEATURE:
<223> OTHER INFORMATION: RT PCR primer for ONSEN from Arabidopsis
      thaliana

<400> SEQUENCE: 10
ttagtataag gctgagctgg aaactg                                 26

<210> SEQ ID NO 11
<211> LENGTH: 23
<212> TYPE: DNA
<213> ORGANISM: Artificial Sequence
<220> FEATURE:
<223> OTHER INFORMATION: RT PCR primer for ONSEN from Arabidopsis
      thaliana

<400> SEQUENCE: 11
caagcctaac cctcagctac atg                                    23

<210> SEQ ID NO 12
<211> LENGTH: 25
<212> TYPE: DNA
<213> ORGANISM: Artificial Sequence
<220> FEATURE:
<223> OTHER INFORMATION: Northern Blot probe for the detection of ONSEN
      from Arabidopsis thaliana

<400> SEQUENCE: 12
aagtggtatc agagcttgaa gatcc                                  25

<210> SEQ ID NO 13
<211> LENGTH: 28
<212> TYPE: DNA
<213> ORGANISM: Artificial Sequence
<220> FEATURE:
<223> OTHER INFORMATION: Northern Blot probe for the detection of ONSEN
      from Arabidopsis thaliana

<400> SEQUENCE: 13
```

```
caacaccccc tcttaaactt gattttgc                                                28

<210> SEQ ID NO 14
<211> LENGTH: 24
<212> TYPE: DNA
<213> ORGANISM: Artificial Sequence
<220> FEATURE:
<223> OTHER INFORMATION: M13 sequencing primer

<400> SEQUENCE: 14
cgccagggtt ttcccagtca cgac                                                    24

<210> SEQ ID NO 15
<211> LENGTH: 22
<212> TYPE: DNA
<213> ORGANISM: Artificial Sequence
<220> FEATURE:
<223> OTHER INFORMATION: M13 sequencing primer

<400> SEQUENCE: 15
tcacacagga aacagctatg ac                                                      22

<210> SEQ ID NO 16
<211> LENGTH: 23
<212> TYPE: DNA
<213> ORGANISM: Artificial Sequence
<220> FEATURE:
<223> OTHER INFORMATION: chopPCR primer for ONSEN from Arabidopsis
      thaliana

<400> SEQUENCE: 16
ggttgaaggg tyaaagagta aat                                                     23

<210> SEQ ID NO 17
<211> LENGTH: 25
<212> TYPE: DNA
<213> ORGANISM: Artificial Sequence
<220> FEATURE:
<223> OTHER INFORMATION: chopPCR primer for ONSEN from Arabidopsis
      thaliana

<400> SEQUENCE: 17
cctccaaact acaaaatatc taaaa                                                   25

<210> SEQ ID NO 18
<211> LENGTH: 27
<212> TYPE: DNA
<213> ORGANISM: Artificial Sequence
<220> FEATURE:
<223> OTHER INFORMATION: chopPCR primer for Actin2 from Arabidopsis
      thaliana

<400> SEQUENCE: 18
tgtagtgtcg tacgttgaac agaaagc                                                 27

<210> SEQ ID NO 19
<211> LENGTH: 23
<212> TYPE: DNA
<213> ORGANISM: Artificial Sequence
<220> FEATURE:
<223> OTHER INFORMATION: chopPCR primer for Actin2 from Arabidopsis
      thaliana

<400> SEQUENCE: 19
ttggcacagt gtgagacaca cca                                                     23
```

<210> SEQ ID NO 20
<211> LENGTH: 24
<212> TYPE: DNA
<213> ORGANISM: Artificial Sequence
<220> FEATURE:
<223> OTHER INFORMATION: PCR primer for Houba from rice

<400> SEQUENCE: 20
atcctgggaa gaacaaacca ttaa                                          24

<210> SEQ ID NO 21
<211> LENGTH: 24
<212> TYPE: DNA
<213> ORGANISM: Artificial Sequence
<220> FEATURE:
<223> OTHER INFORMATION: PCR primer for Houba from rice

<400> SEQUENCE: 21
gagttcgagt accttagcca tggt                                          24

<210> SEQ ID NO 22
<211> LENGTH: 20
<212> TYPE: DNA
<213> ORGANISM: Artificial Sequence
<220> FEATURE:
<223> OTHER INFORMATION: PCR primer for chloroplast DNA from rice

<400> SEQUENCE: 22
acaaccactg atgaaggatt                                               20

<210> SEQ ID NO 23
<211> LENGTH: 20
<212> TYPE: DNA
<213> ORGANISM: Artificial Sequence
<220> FEATURE:
<223> OTHER INFORMATION: PCR primer for chloroplast DNA from rice

<400> SEQUENCE: 23
agaaagaaaa gcaacgactg                                               20

<210> SEQ ID NO 24
<211> LENGTH: 20
<212> TYPE: DNA
<213> ORGANISM: Artificial Sequence
<220> FEATURE:
<223> OTHER INFORMATION: PCR primer for ONSEN from Arabidopsis thaliana

<400> SEQUENCE: 24
acctagctct gagtgatgaa                                               20

<210> SEQ ID NO 25
<211> LENGTH: 21
<212> TYPE: DNA
<213> ORGANISM: Artificial Sequence
<220> FEATURE:
<223> OTHER INFORMATION: PCR primer for ONSEN from Arabidposis thaliana

<400> SEQUENCE: 25
tggatataca cattggttgc a                                             21

<210> SEQ ID NO 26
<211> LENGTH: 20
<212> TYPE: DNA
<213> ORGANISM: Artificial Sequence
<220> FEATURE:
<223> OTHER INFORMATION: PCR primer for ONSEN from Arabidopsis thaliana

```
<400> SEQUENCE: 26
ggagaaagct gaaaacttgg                                               20

<210> SEQ ID NO 27
<211> LENGTH: 20
<212> TYPE: DNA
<213> ORGANISM: Artificial Sequence
<220> FEATURE:
<223> OTHER INFORMATION: PCR primer for ONSEN from Arabidopsis thaliana

<400> SEQUENCE: 27
ctaggttggt gactgatgag                                               20

<210> SEQ ID NO 28
<211> LENGTH: 20
<212> TYPE: DNA
<213> ORGANISM: Artificial Sequence
<220> FEATURE:
<223> OTHER INFORMATION: PCR primer for ONSEN from Arabidopsis thaliana

<400> SEQUENCE: 28
aagaatggga gcagcattaa                                               20

<210> SEQ ID NO 29
<211> LENGTH: 20
<212> TYPE: DNA
<213> ORGANISM: Artificial Sequence
<220> FEATURE:
<223> OTHER INFORMATION: PCR primer for ONSEN from Arabidopsis thaliana

<400> SEQUENCE: 29
gcagtactat aaccgggact                                               20

<210> SEQ ID NO 30
<211> LENGTH: 20
<212> TYPE: DNA
<213> ORGANISM: Artificial Sequence
<220> FEATURE:
<223> OTHER INFORMATION: PCR primer for ONSEN from Arabidopsis thaliana

<400> SEQUENCE: 30
gaactttccg ttgttaccgg                                               20

<210> SEQ ID NO 31
<211> LENGTH: 20
<212> TYPE: DNA
<213> ORGANISM: Artificial Sequence
<220> FEATURE:
<223> OTHER INFORMATION: PCR primer for ONSEN from Arabidopsis thaliana

<400> SEQUENCE: 31
atgagacagg gagcttatct                                               20

<210> SEQ ID NO 32
<211> LENGTH: 20
<212> TYPE: DNA
<213> ORGANISM: Artificial Sequence
<220> FEATURE:
<223> OTHER INFORMATION: PCR primer for ONSEN from Arabidopsis thaliana

<400> SEQUENCE: 32
ggtgtgaacc gaacctaaat                                               20

<210> SEQ ID NO 33
```

```
<211> LENGTH: 20
<212> TYPE: DNA
<213> ORGANISM: Artificial Sequence
<220> FEATURE:
<223> OTHER INFORMATION: PCR primer for ONSEN from Arabidopsis thaliana

<400> SEQUENCE: 33
aaacaccaga aatctttcgc                                                  20

<210> SEQ ID NO 34
<211> LENGTH: 23
<212> TYPE: DNA
<213> ORGANISM: Artificial Sequence
<220> FEATURE:
<223> OTHER INFORMATION: PCR primer for Houba from rice

<400> SEQUENCE: 34
ggttgaaggg tyaaagagta aat                                              23

<210> SEQ ID NO 35
<211> LENGTH: 25
<212> TYPE: DNA
<213> ORGANISM: Artificial Sequence
<220> FEATURE:
<223> OTHER INFORMATION: PCR primer for Houba from rice

<400> SEQUENCE: 35
cctccaaact acaaaatatc taaaa                                            25

<210> SEQ ID NO 36
<211> LENGTH: 24
<212> TYPE: DNA
<213> ORGANISM: Artificial Sequence
<220> FEATURE:
<223> OTHER INFORMATION: PCR primer for Houba from rice

<400> SEQUENCE: 36
atcctgggaa gaacaaacca ttaa                                             24

<210> SEQ ID NO 37
<211> LENGTH: 24
<212> TYPE: DNA
<213> ORGANISM: Artificial Sequence
<220> FEATURE:
<223> OTHER INFORMATION: PCR primer for Houba from rice

<400> SEQUENCE: 37
gagttcgagt accttagcca tggt                                             24
```

MOBILISATION OF TRANSPOSABLE ELEMENTS TO ENHANCE GENETIC AND EPIGENETIC VARIABILITY IN A POPULATION

CROSS-REFERENCE TO RELATED APPLICATIONS

This is the U.S. National Stage of International Patent Application No. PCT/EP2016/079276 filed on Nov. 30, 2016, which was published in English under PCT Article 21(2), and which in turn claims the benefit of European Patent Application No. 15197663.6 filed on Dec. 2, 2015.

FIELD OF THE INVENTION

The present invention relates to the mobilisation of transposable elements and related uses thereof.

BACKGROUND OF THE INVENTION

Transposable elements (TEs) were initially discovered in the early 1950s by Barbara McClintock due to their mutagenic activity that could influence kernel pigmentation (variegation) in maize (McClintock, PNAS, 1950 36(6):344-55). Since their initial discovery numerous functions have been attributed to TEs. Indeed, TEs now tend to be viewed as natural molecular tools that can reshape the genome (Bire et al., Methods Mol Biol, 2012; 859:1-28). TEs have been identified in playing important (if not major) roles in structuring host genomes; especially centromeric regions are rich in TEs. The copy number of long terminal repeats (LTR) retrotransposons has been found to strongly correlate with host genome size and mobilization of TEs can have an impact on genome organization by inducing chromosome breakage and by influencing homologous recombination. At the gene level, TEs can have multiple effects: Cause mutations by directly inserting into genes, move genes within the genome, duplicate and/or create novel genes, regulate gene expression, create novel regulatory pathways and bring genes under epigenetic control. Currently, TEs are considered as a mutagen that can accentuate the positive outcome of the mutagenesis to the host (Bennetzen et al, Annu Rev Plant Biol, 2014, 65:505-30).

TEs have proven to be very useful genetic tools and have been broadly exploited for gene disruption and transgenesis in a wide variety of organisms. However, because TEs naturally very rarely get activated under normal growth conditions only few active TEs are currently known. Thus only a very limited number of TEs are actively being used for genetic modification. Some examples include P elements (Drosophila), PiggyBac (insects, human cell lines), L1 LINE elements (mouse), Mariner (vertebrates), Sleeping-Beauty (animals). In order to create genetic diversity, these TEs are introduced into the organisms of interest via transgenesis. However, this limits use of organisms modified in such a manner because they are considered as genetically modified organisms (GMOs) by current legislation.

In plants, it has been demonstrated that the mobility of transposable elements is limited by DNA methylation and certain histone marks (Miura et al., Nature, 2001, 411(6834): 212-4; Mirouze et al., Nature, 2009, 461(7262):427-30). Suppression of DNA methylation in genetic mutants can therefore result in the mobilization of transposable elements. It was also shown that drugs that reduce DNA methylation (e.g. 5-aza-2'-deoxycytidine) can mobilize certain DNA TEs (Scortecci et al., Plant Cell Physiol, 1997, 38(3):336-43). Furthermore, it has been reported that stresses on plants defective in RNA-directed DNA methylation (RdDM) activate transposable elements (Ito, H. et al., Nature, 2011, 472:115-19). However, the requirement of genetic mutants in components involved in the defense against TEs is limiting the possibility to activate TEs in non-model organisms or organisms that are difficult to transform. Therefore, the exploitation of endogenous TEs to obtain genetic and epigenetic diversity is currently very limited.

Under normal growth conditions, TEs are very rarely mobilized and different treatments to activate TEs have so far been very inefficient in eukaryotes. Treatments with drugs that reduce genomic DNA methylation levels have been shown to allow mild activation of TEs (Baubec, T. et al., Plant J, 2009 57:542-54), but without resulting in novel insertions of those TEs. It has been shown in plants that mutations in factors involved in the RNA-directed DNA methylation pathway could mobilize TEs at a high frequency. An important limitation in these approaches is that they are either inefficient (aforementioned drug treatment) or they require genetic mutations that are difficult to obtain, especially in non-model organisms. These technical problems therefore limit the use and the study of transposable elements in most organisms.

The problem underlying the present invention is to provide the means for efficient mobilization of transposable elements. This problem is solved by the subject-matter of the independent claims.

SPECIFIC DESCRIPTION OF THE INVENTION

The inventors provide herein a drug-based treatment that can mobilize transposable elements in eukaryotes. Additionally, the combination of this treatment with specific stresses leads to the mobilization of specific TEs that respond to this particular stress. The treatment leads to a high accumulation of extrachromosomal DNA of the activated TEs in the treated organism. Furthermore, the progeny of the treated organism shows stable integration of a high number of TE copies in the genome and increased resistance to the stress that is part of the treatment. Therefore, the method of the invention overcomes the necessity of genetic mutations to inactivate TE defense, thus allowing transposable elements to be efficiently activated in virtually any eukaryote. This invention enables the induction of TE mediated changes in genome size and structure, modulation of endogenous gene expression, gene transduplication, heterosis, homologous recombination and stress adaptation. Furthermore, this invention allows the identification of novel functional TEs.

According to a first aspect of the invention a method for the mobilization of a transposable element, particularly within the genome, of a eukaryotic cell is provided. The method comprises:
a) providing a eukaryotic cell comprising one or several dormant, i.e. inactive, transposable elements, and
b) contacting the cell(s) with an inhibitor of transcription, and optionally, contacting the cell additionally with an inhibitor of DNA-methylation, thereby yielding a eukaryotic cell with one or several mobilized transposable elements.

In the context of the present specification the terms transposable element or transposons are used in their meaning known in the art of molecular genetics; they refer to DNA sequences in the genome of an organism that are able to change their position within the genome (cut and paste mechanism) or being able to produce novel copies of themselves that integrate into the genome (copy and paste mechanism). Transposition can result in multiplication of the element thereby influencing the size of the genome. There are two classes of transposons, class 1 transposons also referred to as retrotransposons and class 2 transposons also referred to as DNA transposons. Retrotransposons are first transcribed into RNA by the molecular apparatus provided by the host cell, and are then reverse transcribed into a double stranded DNA copy of the RNA, termed complementary DNA (cDNA) before they are inserted at a new position into the genome. They share some characteristics such as the dependency on a reverse transcriptase with retroviruses. DNA transposons do not have a RNA intermediate and are transferred to their new position in the genome by a transposase. The majority of transposons in the genome are inactive and will not duplicate or change position. The activation of transposons is therefore also referred to as mobilization of transposons. Examples of transposons that are responsive to certain stresses are provided in Table 1. These transposons are activated by the indicated stress up to a certain degree. However, use of the method of the invention mobilizes these transposons to a much larger extent as can be seen in the examples provided.

In certain embodiments of any aspect of the invention, a class 1 transposon is mobilized.

In certain embodiments of any aspect of the invention, a class 2 transposon is mobilized.

In the context of the present specification the term DNA methylation is used in its meaning known in the art of molecular biology and molecular genetics; it refers to the addition of methyl groups to the DNA, which in eukaryotes occurs mainly on cytosines. Methylation of DNA is catalyzed by DNA methyltransferases (DNMT) and can be divided into maintenance methylation, which is necessary to transfer methylation patterns on newly synthesized DNA strands, and de novo methylation. DNA-methylation is associated with the inactivation of gene expression and the silencing of transposons. DNA methylation can be passed on to following generations and therefore represents a common form of epigenetic modification.

In the context of the present specification the term exogenous compound refers to molecules that are not present in the cell under physiological conditions unless added technically.

In certain embodiments, the inhibitor of DNA methylation might be present in at least some of the cells under at least some particular physiological conditions in trace amounts, but is added in the method of the invention at much higher concentrations to exert a significant impact on cell physiology. To achieve this, the compound is present in the cell's medium at a concentration being selected to be at least 10 times higher than the concentration of the inhibitor of DNA methylation found in the interior of the cell.

In certain embodiments, the inhibitor of transcription is present in the cell under physiological conditions and present in a medium at a concentration being selected to be at least 10 times, 100 times, 1000 times, or even 10.000 times higher than the concentration of the inhibitor of transcription found in the interior of the cell.

In certain embodiments, the method of the invention as specified in any aspect or embodiment disclosed herein additionally comprises a step c):

c) exposing the cell to an abiotic stress, biotic stress or chemical stress.

In the context of the present specification the term abiotic stress refers to the negative impact of non-living factors on a living organism in a specific environment. The non-living variable influences the environment beyond its normal range of variation. Non-limiting examples of abiotic stress are heat, cold, drought, submergence/water excess, wind, UV-radiation, nuclear radiation, salinity, heavy metals, soil pH, tissue culture cultivation and starvation of phosphorous, nitrogen, light, $CO_2$ etc. In contrast the term biotic stress refers to the negative impact of fungi, bacteria, viruses, insects, wounding by herbivores and biological competition etc.

The term chemical stress refers to the negative impact of chemical substances ("stressors") on a living organism. These substances may also comprise substances that are

TABLE 1

Examples of transposons

| Transposable element | Activating stress | Organism | Reference |
|---|---|---|---|
| ONSEN | heat, flagellin | *Arabidopsis thaliana* | Ito et al., 2011, Nature; Yu et al., 2012, PNAS |
| TLC1.1 | salicylic acid, abscisic acid, methyl jasmonate, hydrogen peroxide and the synthetic auxin 2,4-D. | *Solanum chilense* | Salazar et al., 2007, Plant Cell |
| Tnt1A | wounding, biotic elicitors and pathogen attacks of fungal extracts | *Nicotiana tabacum* | Melayah et al., 2001, Plant Journal |
| Erika1 Sabrina | heat, drought and wounding cell culture | *Hordeum vulgare* | Alzohairy, et al., 2012; Life Science Journal |
| Tcs1 | cold | *Citrus sinensis* | Butelli et al., 2012; Plant Cell |

In certain embodiments, the inhibitor of DNA methylation is an exogenous compound.

In certain embodiments, the inhibitor of transcription is an exogenous compound.

In certain embodiments, the exogenous compound is a small molecule compound having a molecular mass of ≤1000 u, particularly ≤920 u.

stress-mimicking substances that mimic an abiotic or biotic stress. Non-limiting examples of chemical stressors are herbicides, herbicide safener, insecticides, fungicides, plant secondary metabolites, synthetic or natural compounds that induce plant defense.

The term herbicide safener refers to a compound that selectively protects monocotyledonous plants from herbicide damage whereas dicotyledonous plants are still affected by the herbicides. The common crop plants such as rice, wheat, maize etc but also forage grass, sugar cane and bamboo are monocotyledonous plants whereas most weed species are dicotyledonous plants. Herbicide safeners can be applied as a dressing for the seeds before sowing, to prepare the soil of agricultures or be applied to the foils of grown plants. In the two latter cases herbicide safeners can be applied together with the herbicides. Examples of common herbicide safeners are: Benoxacor (CAS 98730-04-2), Cloquintocet-mexyl (CAS 99607-70-2), Cyometrinil (CAS 63278-33-1), Dichlormid (CAS 37764-25-3), Fenchlorazole-ethyl (CAS 103112-35-2), Fenclorim (CAS 3740-92-9), Flurazole (CAS 72850-64-7), Fluxofenim (CAS 88485-37-4), Furilazole (CAS 121776-33-8), Mefenpyr-diethyl (CAS 135590-91-9), MG 191 (CAS 96420-72-3), Naphthalic anhydride (CAS 81-84-5), MON-13900 (CAS 121776-33-8), LAB 145138 (CAS 79260-71-2) and Oxabetrinil (CAS 74782-23-3).

In certain embodiments, the transposable element is a retrotransposon.

In certain embodiment, the cell is part of a multicellular organism. In certain embodiments, the eukaryotic cell is part of a non-human organism.

In certain embodiments, the eukaryotic cell is a plant cell. In certain embodiments, the plant cell is a cell from *Arabidopsis*, particularly *Arabidopsis thaliana*.

In certain embodiments, the plant cell is part of crop plants, particularly of the family of Poaceae that comprises plants such as rice, sugar cane, maize, wheat, rye, barley, oat or millet. In certain embodiments, the method comprises a subsequent step of isolating said cell and determining whether a phenotype of the cell has been changed.

In certain embodiments, the eukaryotic cell is part of a multicellular organism, particularly a plant, and wherein subsequent to exposure of the cell to step c), the cell is cultivated to render a multicellular organism, and the phenotype of the multicellular organism is determined.

In certain embodiments, the phenotype of the organism comprises determining resistance to the stressor, wherein the stressor causes the stress applied in step c).

In certain embodiments, the resistance to the stressor that causes the stress applied in step c) is increased after application of the method of the invention.

According to a second aspect of the invention a method for increasing genetic and/or epigenetic variation in a population of eukaryotic organisms is provided. The method comprises:
 i. providing an eukaryotic organism,
 ii. contacting the eukaryotic organism with
  an inhibitor of DNA methylation, and/or
  an inhibitor of transcription,
 iii. propagating the eukaryotic organism, yielding the eukaryotic population with increased genetic and/or epigenetic variation.

The method mobilizes dormant, i.e. inactive, not currently transcribed or reverse transcribed, transposable elements within the eukaryotic organism. Since to the knowledge of the inventors, all eukaryotic organisms comprise dormant transposable elements within their genome, the element "eukaryotic organism" is synonymous with "eukaryotic organism comprising a dormant transposable element".

In certain embodiments, the method is employed on a eukaryotic organism comprising any one of the specific transposable elements recited in the current specification.

In certain embodiments of the second aspect of the invention, the method additionally comprises a step ii.a, which is following step ii.:

ii.a exposing the eukaryotic organism to an abiotic stress, biotic stress or chemical stress.

In certain embodiments, the inhibitor of DNA methylation and/or the inhibitor of transcription are provided as a solution in a polar solvent, in particular a polar aprotic solvent, more particularly Dimethyl sulfoxide (DMSO).

In certain embodiments, the inhibitor of DNA methylation and/or the inhibitor of transcription are provided as a solution in a polar solvent, in particular water.

In certain embodiments, the method comprises the subsequent step iv. comprising:
 a. Determining any genetic and/or epigenetic changes or
 b. Determining any changes in the phenotype, particularly the resistance to any stressors applied in step ii.a
  wherein these changes are determined in the individual constituent eukaryotic organisms or for a representative sample of the population of eukaryotic organisms, or for all of the constituent eukaryotic organisms of the population.

In certain embodiments of the first and the second aspect of the invention, the abiotic stress is selected from heat, cold, drought, submergence/water excess, wind, UV-radiation, nuclear radiation, salinity, heavy metals, soil pH, tissue culture cultivation and starvation (phosphorous, nitrogen, light, $CO_2$ etc.).

In certain embodiments of the first and the second aspect of the invention, the biotic stress is selected from the negative impact of fungi, bacteria, viruses, insects, wounding by herbivores and biological competition. Non-limiting examples of fungi having a negative impact would be *Phytophthora infestans* (potato blight) and *Magnaporthe grisea* (rice blast). Non-limiting examples for bacteria having a negative impact are *Botrytis cinerea* (gray mold), *Xylella fastidiosa* (Olive Quick Decline Syndrome) and *Puccinia* spp. (wheat rust). Non-limiting examples of viruses having a negative impact are Tobacco mosaic virus and Tomato spotted wilt virus. Non-limiting examples for insects having a negative impact are *Mamestra brassicae* (Cabbage moth), *Helicoverpa zea* (corn earworm) and *Ostrinia nubilalis* (European corn borer). Non limiting examples of other organisms that can have a negative impact due to biological competition are *Orobanche* (broomrape) and *Ambrosia trifida* (giant ragweed).

In certain embodiments of the first and second aspect of the invention, the chemical stress is selected from herbicides, herbicide safener, insecticides, fungicides, plant secondary metabolites, synthetic or natural compounds that induce plant defense. Non-limiting examples of compounds that induce plant defense are flagellin (natural compound, bacterial elicitor; Felix et al., 1999, Plant J.), a 22-amino acid sequence of the conserved N-terminal part of flagellin (flg22), salicylic acid and analogues e.g. Bion® (natural compound with synthetic analogues; (Vlot et al., 2009, Annu. Rev. Phytopathol.; Friedrich et al., 1996, Plant J.)), jasmonic acid and jasmonic methyl ester (natural compounds; Cohen et al., 1993, Phytopathology), ethylene (natural compound; van Loon et al., 2006, Trends Plant Sci.), abscisic acid (natural compound; Mauch-Mani and Mauch, 2005, Curr. Opin. Plant Biol.) and volatiles such as terpenes and green leaf volatiles (natural compounds; reviewed by Unsicker et al., 2009, Curr Opin Plant Biol).

In certain embodiments of the first and the second aspect of the invention, the DNA-methylation inhibitor is a nucleoside analogue.

In certain embodiments of the first and the second aspect of the invention, the DNA-methylation inhibitor is selected from 5-azacytidine, 5-aza-2'-deoxycytidine, 5-fluoro-2'-deoxycytidine, 5,6-dihydro-5-azacytidine and zebularine.

In certain embodiments of the first and the second aspect of the invention, the inhibitor of transcription is a RNA polymerase inhibitor, in particular a RNA polymerase II inhibitor, a RNA polymerase IV inhibitor or a RNA polymerase V inhibitor, more particularly a RNA polymerase II inhibitor.

In certain embodiments of the first and the second aspect of the invention, the RNA polymerase II inhibitor is selected from
   amatoxins, in particular alpha-amanitin (CAS 23109-05-9),
   derivatives of amatoxins, in particular alpha-amanitin oleate,
   nucleoside analogues, in particular 5,6-dichloro-1-beta-D-ribofuranosylbenzimidazole (DRB; CAS 53-85-0),
   actinomycin D (CAS 50-76-0),
   flavopiridol (CAS 146426-40-6),
   triptolide (CAS 38748-32-2).

In certain embodiments of any aspect of the invention disclosed herein, the amatoxin, in particular alpha-amanitin is used with a concentration of 0.0005 µg/ml to 50 µg/ml, in particular 0.001 µg/ml to 25 µg/ml, more particular 0.005 µg/ml to 20 µg/ml, even more particular 0.005 µg/ml to 5 µg/ml.

In certain embodiments of any aspect of the invention disclosed herein, the inhibitor of DNA methylation, in particular zebularine, is used at a concentration of 5 µM to 100 µM, in particular 10 µM to 80 µM, more particular 10 µM to 40 µM, even more particular 20 µM to 40 µM.

In certain embodiments of the second aspect of the invention, the increased genetic and/or epigenetic variation in a plurality of eukaryotic organisms results in increased resistance of the organisms to the abiotic or biotic stress the organisms have been exposed to. In other words the increase in genetic and/or epigenetic variation is not random as for example would be expected from a chemical mutagen. The increase is directed toward resistance against the stress used in the method. For example using the abiotic stress heat would preferentially result in heat-resistant organisms. Without wishing to be bound by theory the inventors assume that transposons are preferentially integrated into the genome in the vicinity of genes thereby creating novel gene regulatory pathways that are able to respond to the previously applied stress. This may lead to genetic variety in genes activated by the respective stress and thereby confers increased resistance to the respective stress.

According to a third aspect of the invention, the use of a composition in a method according to the first and second aspect of the invention is provided. The composition comprises an inhibitor of DNA-methylation and an inhibitor of transcription.

In certain embodiments, the DNA-methylation inhibitor is a nucleoside analogue.

In certain embodiments, the DNA-methylation inhibitor is selected from 5-azacytidine (CAS 320-67-2), 5-aza-2'-deoxycytidine (CAS 2353-33-5), 5-fluoro-2'-deoxycytidine (CAS 10356-76-0), 5,6-dihydro-5-azacytidine (CAS 62488-57-7) and zebularine (CAS 3690-10-6).

In certain embodiments, the inhibitor of transcription is a RNA polymerase inhibitor, in particular a RNA polymerase II inhibitor, a RNA polymerase IV inhibitor or a RNA polymerase V inhibitor, more particularly a RNA polymerase II inhibitor.

In certain embodiments the RNA polymerase II inhibitor is selected from
   amatoxins, in particular alpha-amanitin (CAS 23109-05-9),
   derivatives of amatoxins, in particular alpha-amanitin oleate,
   nucleoside analogues, in particular 5,6-dichloro-1-beta-D-ribofuranosylbenzimidazole (DRB; CAS 53-85-0),
   actinomycin D (CAS 50-76-0),
   flavopiridol (CAS 146426-40-6),
   triptolide (CAS 38748-32-2).

In certain embodiments, the amatoxin, in particular alpha-amanitin is used with a concentration of 0.5 nM to 55 µM, in particular 1 nM to 27.5 µM, more particular 5 nM to 20 µM, even more particular 5 nM to 5 µM.

In certain embodiments of any of the aspects of the invention disclosed herein, the ratio of the molar concentrations of the inhibitor of transcription, in particular alpha-amanitin, to the inhibitor of DNA-methylation, in particular zebularine, is 0.000005 to 11, more particular 0.000125 to 2, even more particular 0.000125 to 0.125.

In certain embodiments, the ratio of the molar concentration depends on the concentrations a and b, which are as follows:
   a) the inhibitor of DNA-methylation, in particular zebularine, is used at a concentration of 5 µM to 100 µM, in particular 10 µM to 80 µM, more particular 10 µM to 40 µM, even more particular 20 µM to 40 µM
   b) amatoxin, in particular alpha-amanitin is used at a concentration of 0.0005 µg/ml to 50 µg/ml, in particular 0.001 µg/ml to 25 µg/ml, more particular 0.005 µg/ml to 20 µg/ml, even more particular 0.005 µg/ml to 5 µg/ml.

A fourth aspect of the invention provides a kit of parts for use in the method according to the first and second aspect of the invention. The kit of parts comprises an inhibitor of DNA-methylation and an inhibitor of transcription.

In certain embodiments, the DNA-methylation inhibitor is a nucleoside analogue.

In certain embodiments, the DNA-methylation inhibitor is selected from 5-azacytidine (CAS 320-67-2), 5-aza-2'-deoxycytidine (CAS 2353-33-5), 5-fluoro-2'-deoxycytidine (CAS 10356-76-0), 5,6-dihydro-5-azacytidine (CAS 62488-57-7) and zebularine (CAS 3690-10-6).

In certain embodiments, the inhibitor of transcription is a RNA polymerase inhibitor, in particular a RNA polymerase II inhibitor, a RNA polymerase IV inhibitor or a RNA polymerase V inhibitor, more particularly a RNA polymerase II inhibitor.

In certain embodiments the RNA polymerase II inhibitor is selected from
   amatoxins, in particular alpha-amanitin (CAS 23109-05-9),
   derivatives of amatoxins, in particular alpha-amanitin oleate,
   nucleoside analogues, in particular 5,6-dichloro-1-beta-D-ribofuranosylbenzimidazole (DRB; CAS 53-85-0),
   actinomycin D (CAS 50-76-0),
   flavopiridol (CAS 146426-40-6),
   triptolide (CAS 38748-32-2).

Wherever alternatives for single separable features such as, for example, a type of inhibitor or organism are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

SHORT DESCRIPTION OF THE FIGURES

FIG. 1 shows accumulation of ONSEN extrachromosomal DNA upon pharmacological treatment and heat stress. (a) ONSEN DNA accumulation measured by qPCR directly after control stress (CS) heat stress (HS)-treatment in wild-type (WT) and nrpb2-3 plants and treatments with alpha-amanitin (A, 5 μg/ml) or zebularine (Z, 10 μM) (mean±s.e.m., n=6 biological repetitions, values relative to ACTIN2). (b) ONSEN copy number measured by quantitative PCR (qPCR) in seedlings of Columbia (Col) WT directly after control stress (CS; 24 h 6° C.), heat stress (HS; 24 h 6° C. and 24 h 37° C.) and a treatment with A (5 μg/ml), Z (40 μM) or a combination thereof (A&Z). (Mean±s.e.m., n=3 biological repetitions). The double treatment (A&Z) leads to a very strong heat-stress dependent activation of ONSEN resulting in up to 700 extrachromosomal ONSEN DNA copies.

Figure 2:
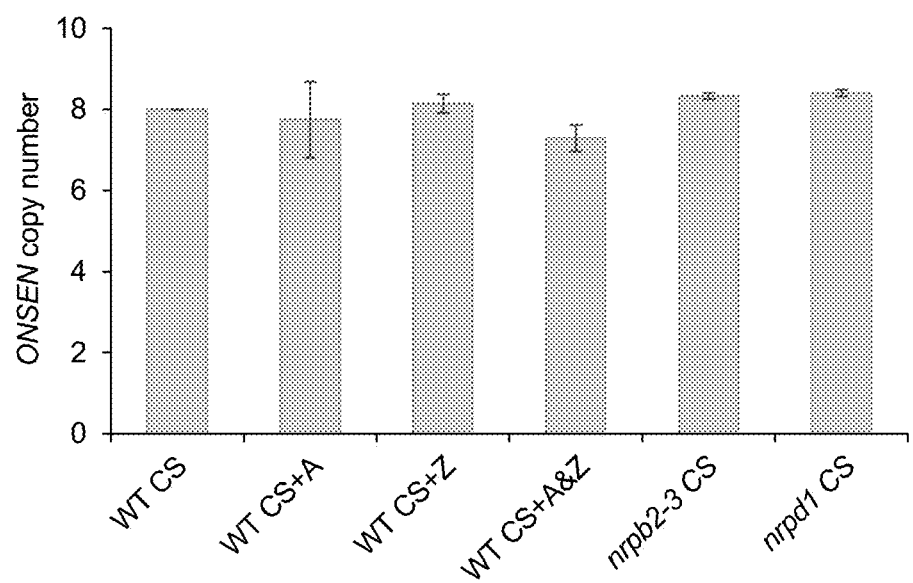

FIG. 2 shows the stress-dependence of ONSEN mobilisation. The graph shows ONSEN copy numbers in *A. thaliana* seedlings after chemical treatment with A (5 μg/ml), Z (40 μM), the combinations of A and Z (A&Z) in WT, nrpb2-3 and nrpd1 plants following the CS. ONSEN copy number measured by qPCR (mean s.e.m., n=3 biological replicates, values relative to ACTIN2). This result shows that the production of ONSEN extrachromosomal DNA is dependent on heat-stress.

FIG. 3 shows that simultaneous inhibition of methyltransferases and Pol II mimics the nrpd1-mutant. (a) Asymmetric methylation analysis of the ONSEN LTR and the soloLTR in untreated and A (5 μg/ml), Z (40 μM) or A&Z-treated seedlings of the WT and the nrpd1 mutant after CS. PCR products obtained from genomic DNA that was used undigested (input) or after digestion with the CHH-methylation sensitive restriction enzyme DdeI. ACTIN2 is included as a control for complete DdeI digestion. The A&Z double treatment with A (5 μg/ml) and Z (40 μM) resulted in a very strong reduction of DNA methylation at ONSEN and soloLTR comparable to the nrpd1 mutant. (b) Northern blot indicating ONSEN-transcription directly after CS, HS and HS plus treatment with A (5 μg/ml), Z (40 μM) or a combination of A&Z in WT and nrpd1 plants. A Midori-stained agarose-gel is shown as a loading control. The level of the full length ONSEN transcript after heat stress and the double treatment with A (5 μg/ml) and Z (40 μM) is comparable to the nrpd1-mutant. (c) Accumulation of ONSEN DNA measured by qPCR in seedlings of WT, rdr6, dcl2/3/4 and nrpd1 plants directly after CS, HS and HS plus treatment with A, Z or a combination of A&Z. This result shows that RNA pot II is active upstream of the DICER-like enzymes.

FIG. 4 shows the drug-induced mobilisation of ONSEN in wild-type *Arabidopsis* plants. (a) Transposon display confirming novel ONSEN insertions in the F2 generation of HS (HS control) and HS and A (5 μg/ml) and Z (40 μM) treated WT plants (HS+A&Z). Integrated ONSEN copies were measured by qPCR (upper part) and detected by transposon display (lower part). ONSEN copy numbers of seven selected individual, non-related plants are depicted. Copy numbers exceeding eight as measured by qPCR (upper part) and the observed additional bands on the transposon display (lower part) in the HS+A&Z treated Col WT plants indicate novel insertions of additional ONSEN copies. M is a 1 kb size marker. (b), ONSEN copy number in the F1, F2 and F3 generation measured by qPCR (n=3 technical replicates, values relative to ACTIN2) Copy numbers >8 in lines 1-7 indicate insertions of additional ONSEN copies. c, and d, photographs of F2-plants containing novel ONSEN insertions showing both homogeneous and stress-dependent phenotypic variability induced by the HS+A&Z treatment when grown under long (c) and short day conditions (d). qPCR-Data for the F3-generation of line 6 in (b) as well as pictures of phenotypes in (c) and (d) are missing due to severe infertility and extinction of this line. Examples for phenotypes observed in of lines with novel ONSEN insertions (lines1-7) include higher biomass under short day conditions (line 3), early flowering under long day conditions (line 7) and reduced chlorophyll accumulation (line 1). In summary this dataset shows that A&Z-treatment leads to an efficient burst of ONSEN transposition. New ONSEN insertions are stably inherited over several generations and cause phenotypic changes.

Figure 5:
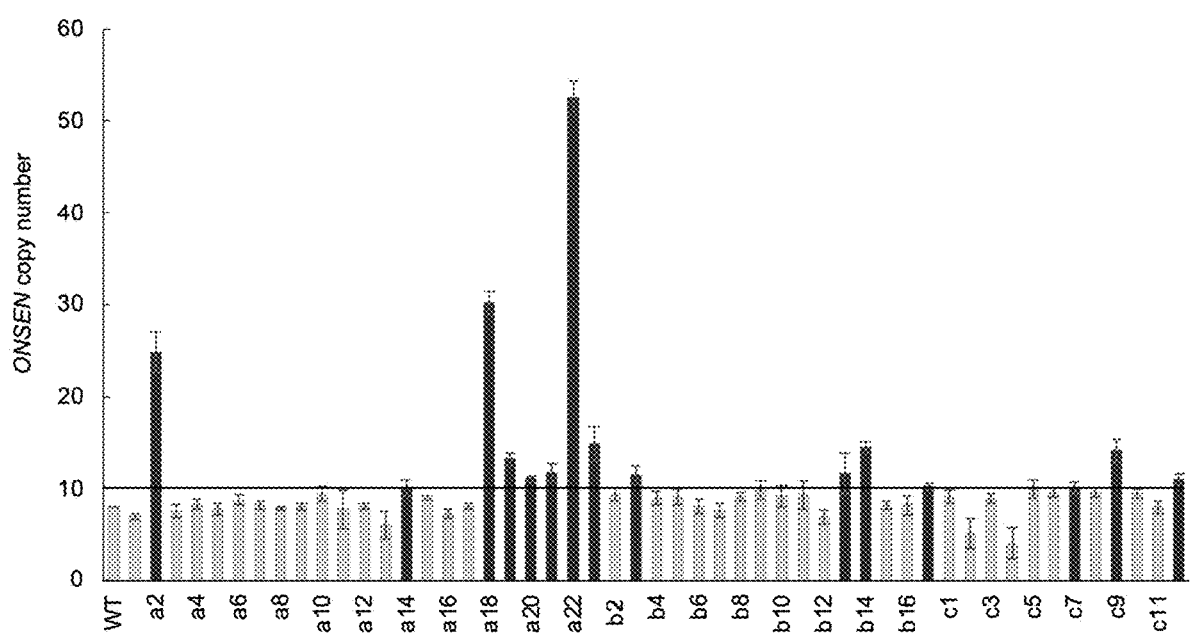

FIG. 5 shows the increase in ONSEN copy numbers in F1 pools of heat-stressed and treated plants. Parental plants were treated and heat stressed in independent experiments (characters a-c) with a combination of A (5 μg/ml) and Z (40 μM). Pools with significantly increased ONSEN-copy numbers (>10) are highlighted in dark grey. ONSEN copy number measured by qPCR (mean±s.e.m., n=3 technical repetitions, values relative to ACTIN2). Approximately 29.4% of tested F1 pools of heat stressed and A+Z treated wild type plants showed a significantly increased ONSEN copy number.

Figure 6A:
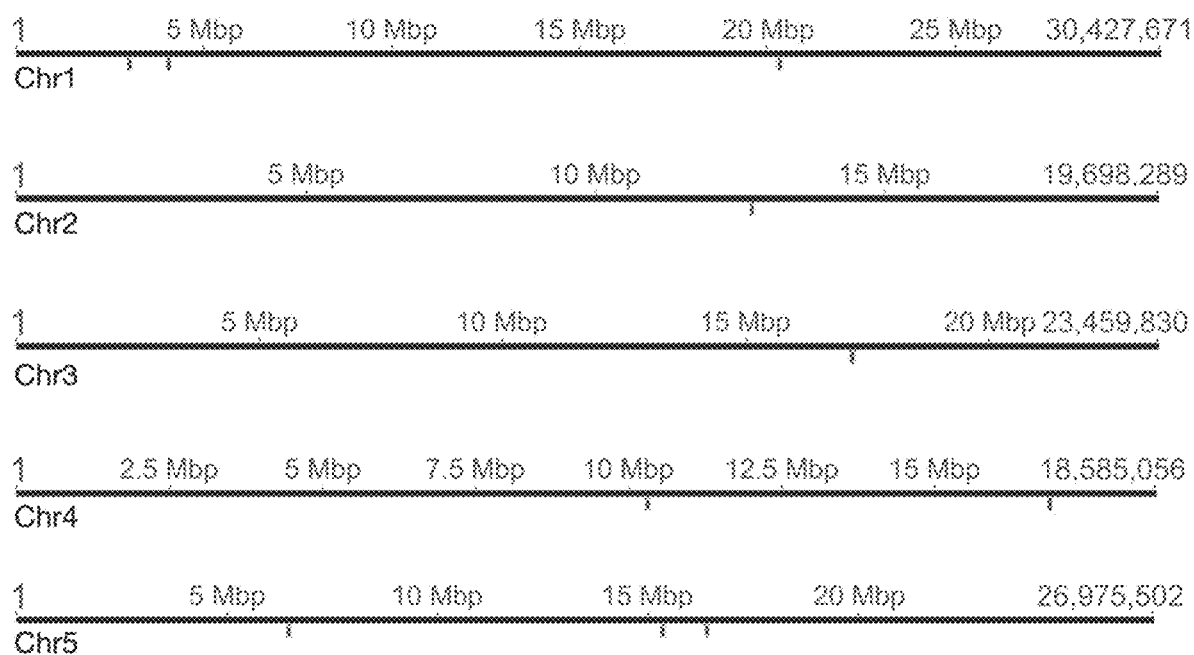
Figure 6B:
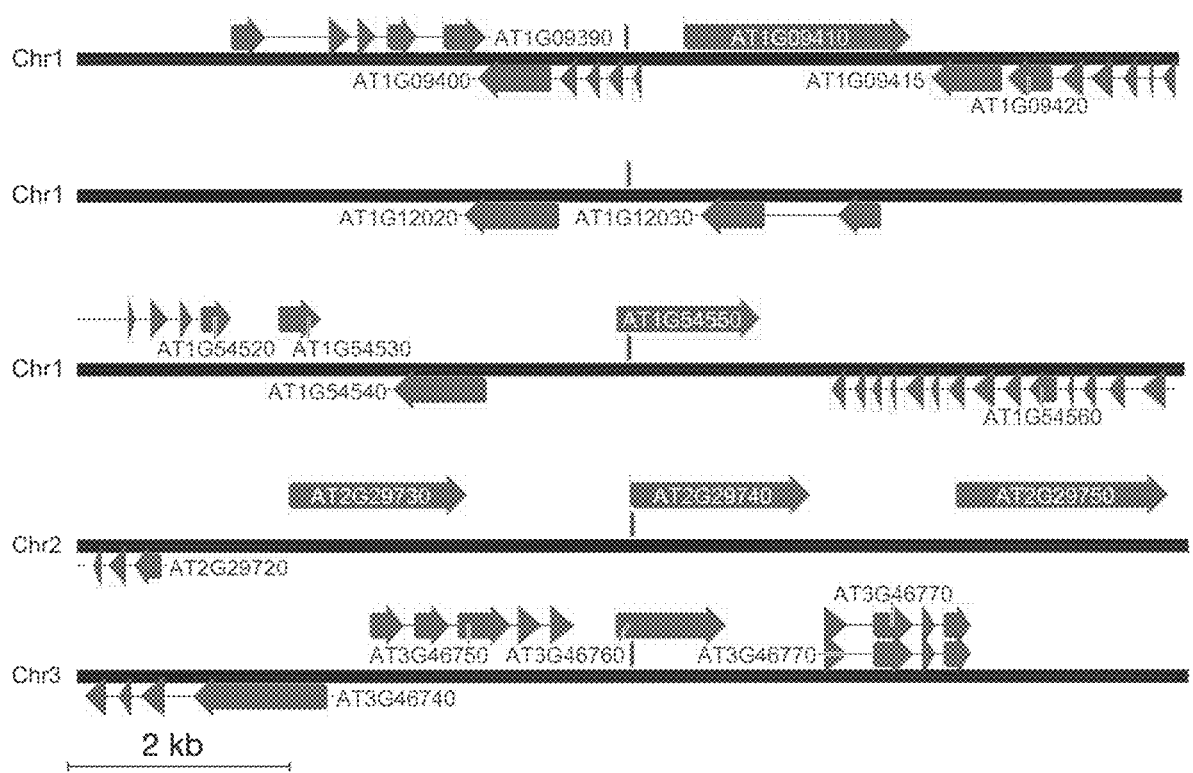
Figure 6B:
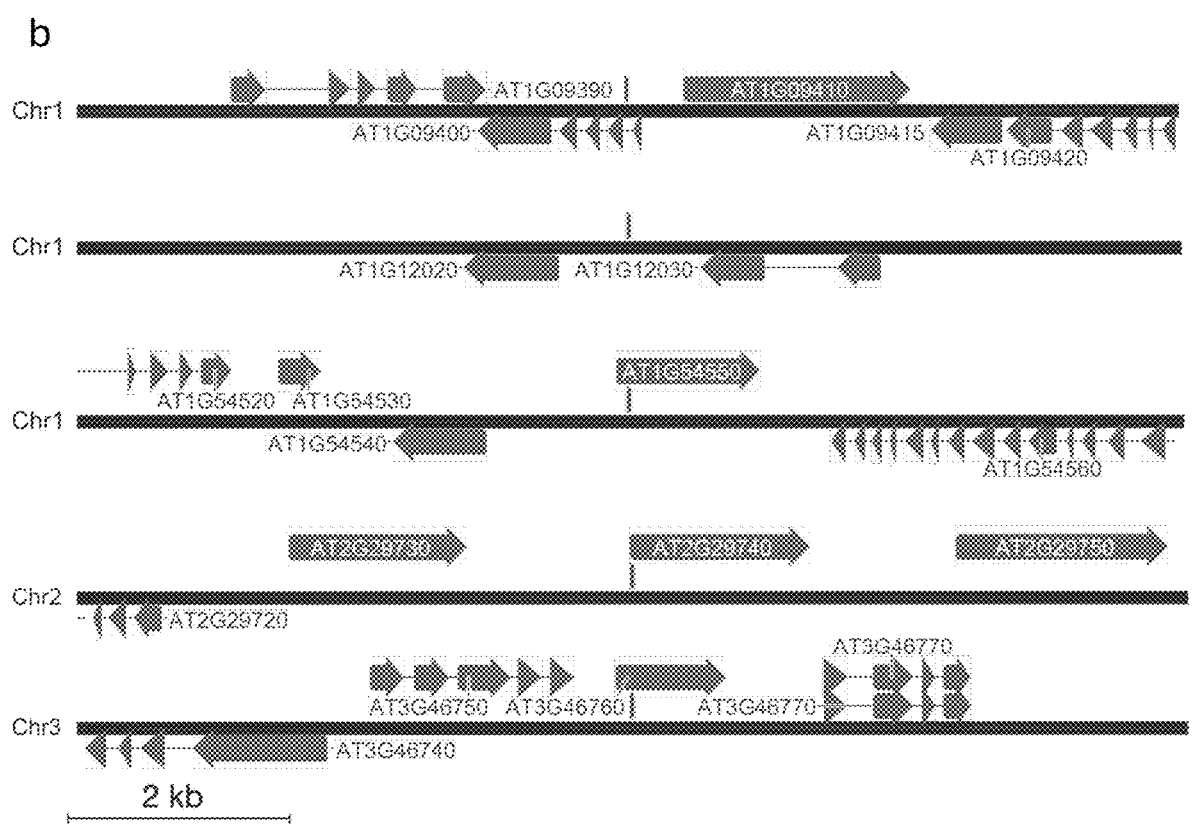

FIG. 6 shows a summary of confirmed novel ONSEN insertions. (a) Genome wide distribution and (b) Close-up of regions with new ONSEN insertions in the F2 generation of a selected HS+A&Z treated WT plant (line #3). Orientation of the ONSEN insertions is indicated central arrows.

FIG. 7 shows the drug-induced activation of the *Houba* retrotransposon in rice (*O. sativa*). Mobilome analysis of DNA extracted from seedlings after growth on control conditions (C), A (5 μg/ml), Z (40 μM), and the combination of A&Z. (a) Detail of the normalized depth of coverage compared to the untreated control plant obtained after aligning the sequenced reads on one *Houba* element. (b) Scheme of primers localization (black ban *Houba* element, arrows: PCR primers, box: LTR). (c) extrachromosomal circular forms of *Houba* are specifically detected in plants treated with both A&Z using inverse PCR with primers shown in 4b. (d) Specific PCR on circular chloroplast DNA is shown as a loading control. Total DNA subjected to a rolling circle amplification was used as a template. These results demonstrate the efficient A&Z-dependent mobilization of the *Houba* transposon in rice.

Figure 8:
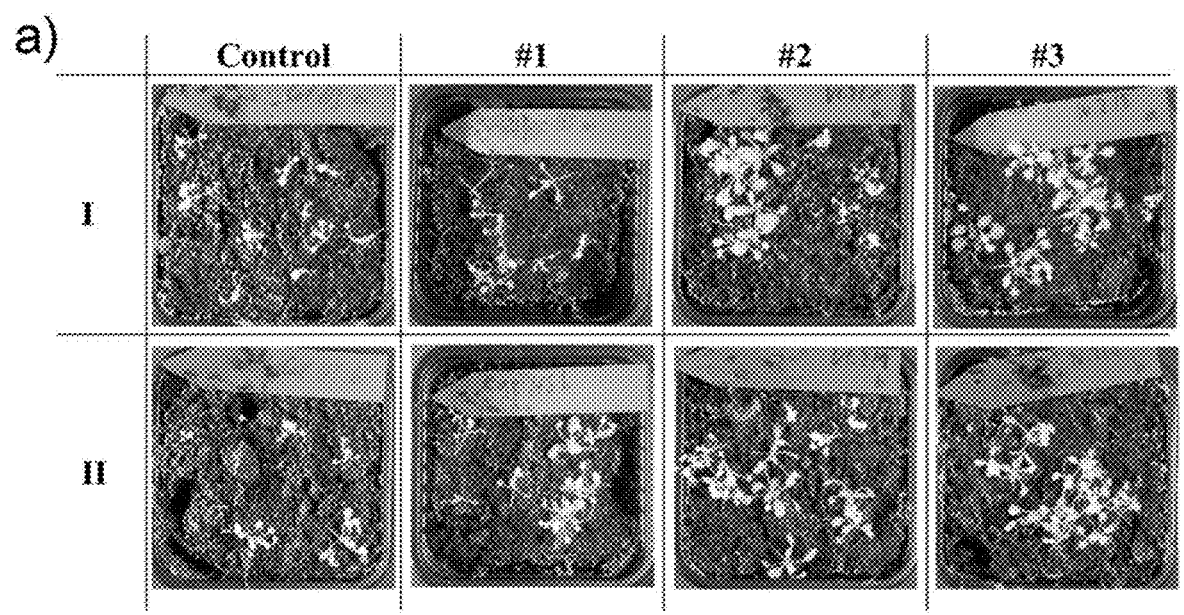
Figure 8:
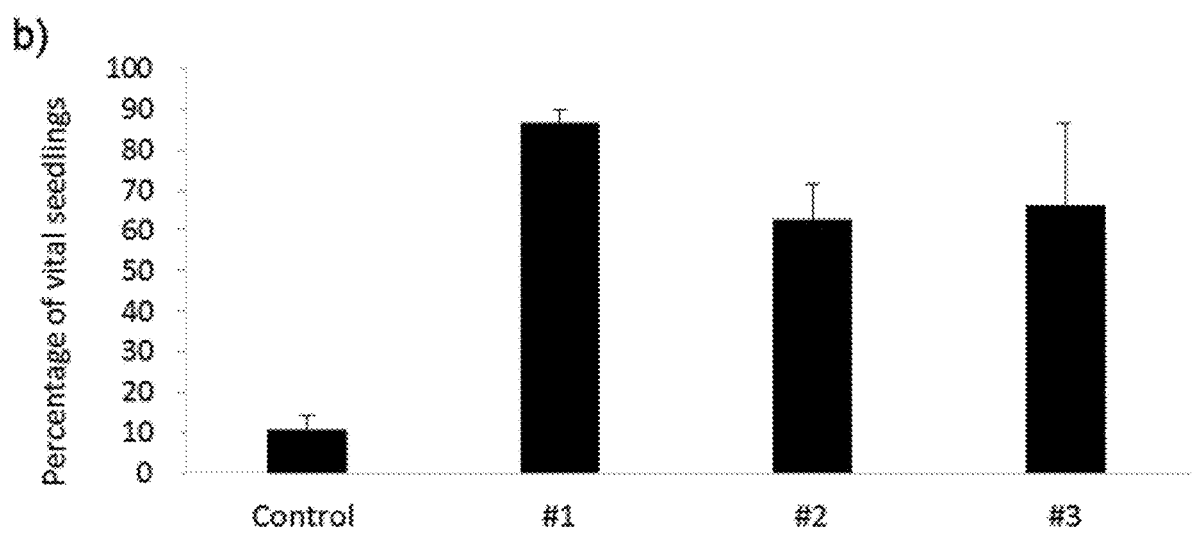

FIG. 8 shows increased heat tolerance in the F2 generation of treated *Arabidopsis* seedlings. Tolerance to repetitive heat stress (42° C.) in the F2 progeny of wildtype plants that were either only heat stressed (control) or heat stressed and treated with A (5 μg/ml) and Z (40 μM) (#1-3). (a) Two biological replicates (I and II) are depicted, (b) Percentage of vital seedlings (Mean±s.e.m., n=2 biological repetitions). F2 seedlings originating from Heat stressed and A&Z-treated plants show a significantly increased heat tolerance (>60% vital seedlings) compared to the F2 of a plant that was only heat stressed (10% vital seedlings). This demonstrates that the A&Z-dependent mobilization of a heat-stress responsive transposon can produce plants that are better adapted to heat stress.

Figure 9:
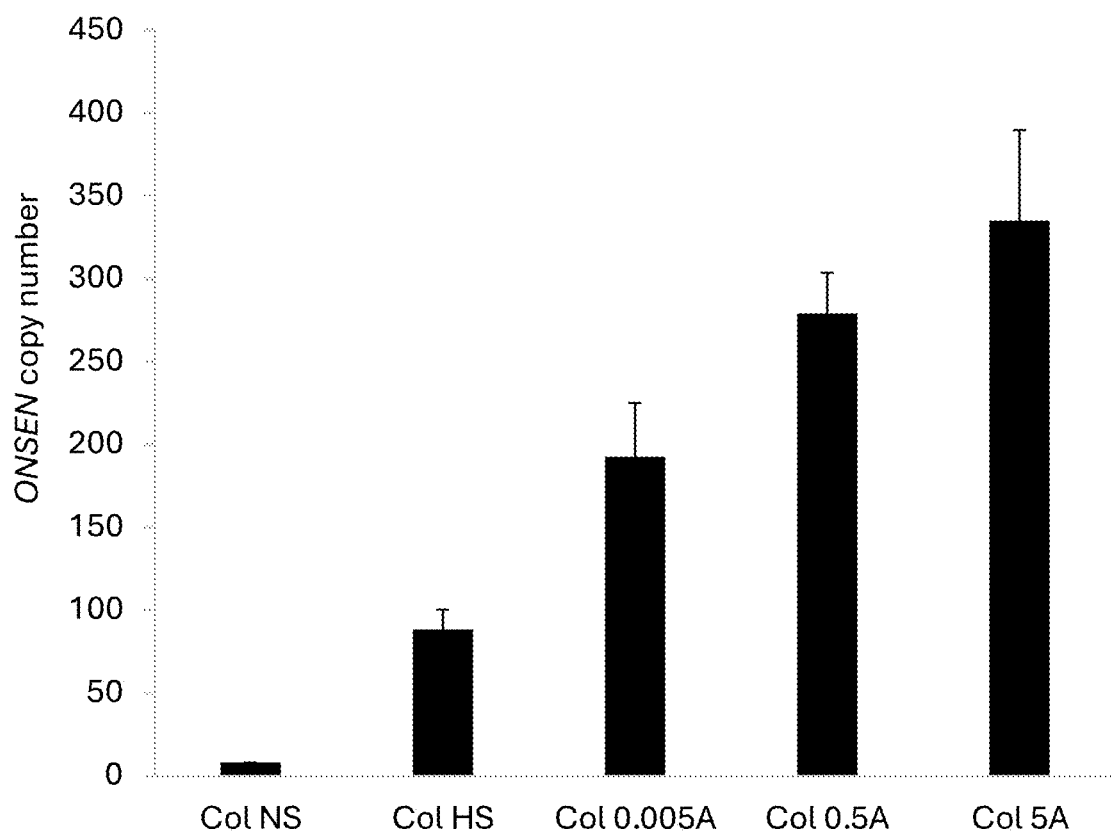

FIG. 9 shows dose dependent accumulation of ONSEN extrachromosomal DNA upon pharmacological treatment and heat stress. ONSEN copy number was measured by qPCR in seedlings of Columbia (Col) wildtype directly after control stress (CS), heat stress (HS) and a treatment with α-amanitin in different concentrations given in μg/ml.

(Mean±s.e.m., n=3 technical repetitions). This shows that the number of mobilized transposons can be regulated by the amount of A used for the treatment.

FIG. 10 shows epigenetic changes at the DNA methylation level induced by the treatment of plants and human cells with A. (a) Midori stained Agarose gel showing reduction of DNA-methylation at the ONSEN LTR upon pharmacological treatment and heat stress in WT (Col) seedlings directly after control stress (CS; 24 h 6° C.), heat stress (HS; 24 h 6° C. and 24 h 37° C.) and a treatment with A (20 µg/ml), Z (10 µM) or a combination thereof (A&Z). Undigested DNA was used as a PCR-template for the loading control (Input). PCR on DdeI-digested DNA shows reduction in DNA-methylation after treatment with A, Z or a combination of A&Z. (b) CHH methylation state at the ONSEN LTR assessed by bisulfite sequencing performed on CS plants grown on medium with or without A. (c) LINE-1 DNA methylation levels assessed in human A549 cancer cells grown in control medium and medium supplemented with 0.5 µg/ml A. This shows that A can be used as a potent DNA demethylating agent in plants and human cells.

Figure 11:
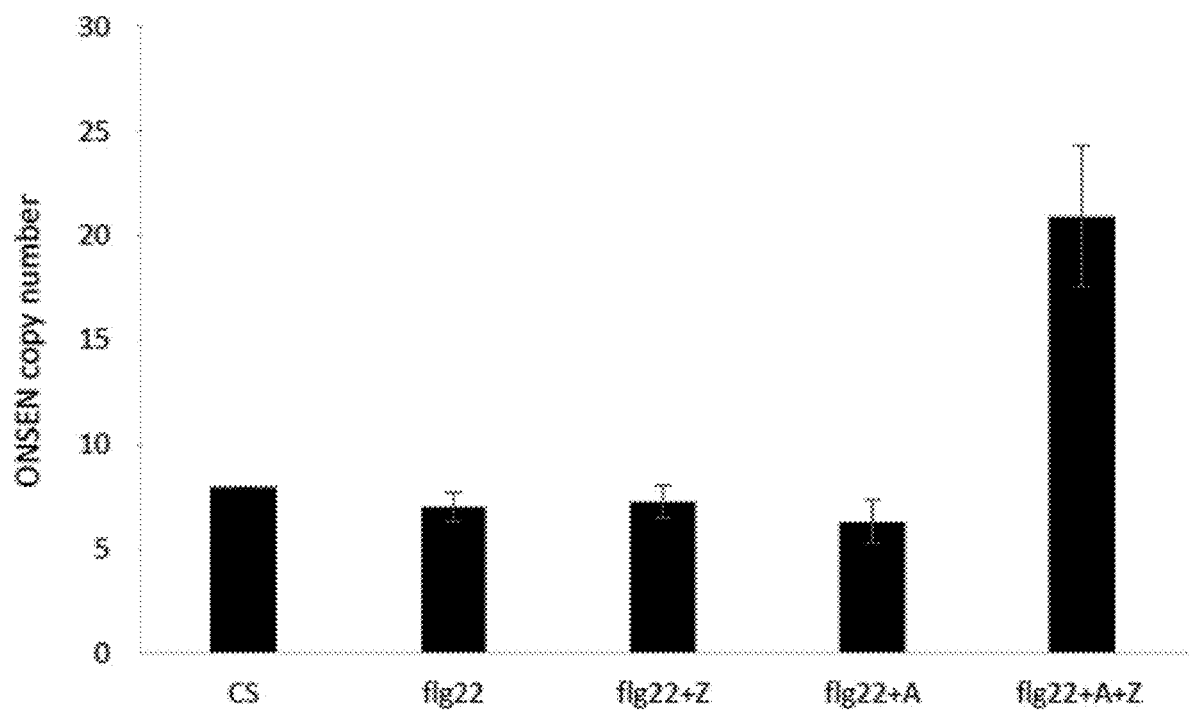

FIG. 11 shows accumulation of ONSEN extrachromosomal DNA upon combined pharmacological and flagellin-treatment. ONSEN copy number measured by quantitative PCR (qPCR) in seedlings of Col wild type directly after control stress, 5 h after treatment with flagellin (flg22) alone or in combination with A (5 µg/ml), Z (40 µM) or a combination thereof (A&Z). (Mean±s.e.m., n=3 technical repetitions).

Figure 12:
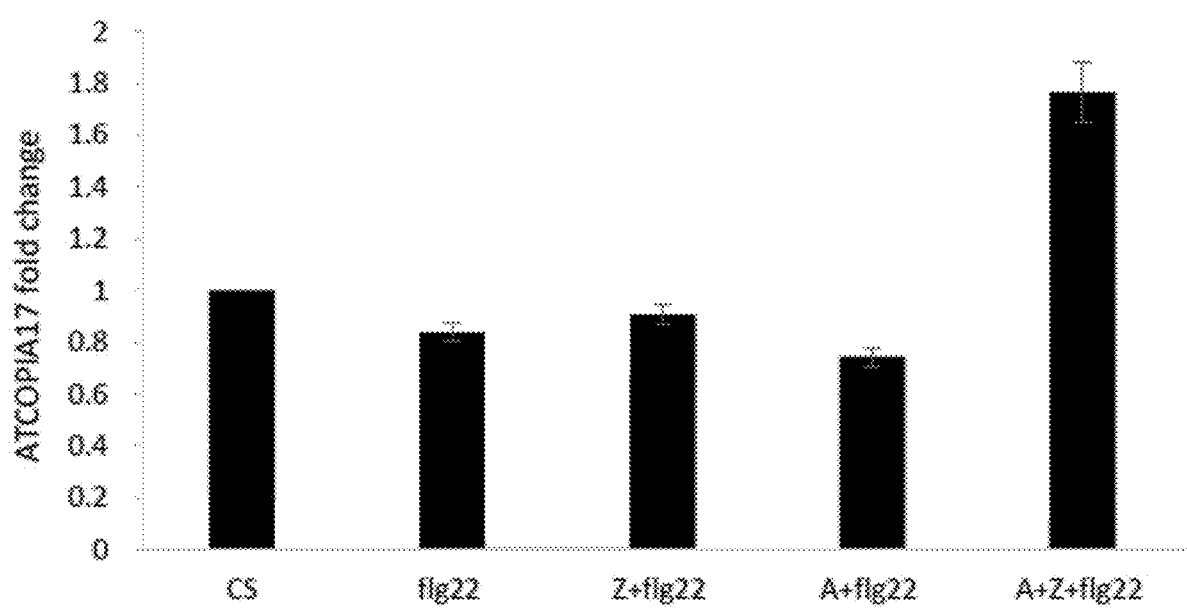

FIG. 12 shows activation of ATCOPIA17 upon combined pharmacological and flagellin-treatment. ATCOPIA17 fold change was measured by quantitative PCR (qPCR) on total DNA in seedlings of the Col wild type directly after control stress, 5 h after treatment with flagellin (flg22) alone or in combination with A (5 µg/ml), Z (40 µM) or a combination thereof (A&Z). (Mean±s.e.m., n=3 technical repetitions).

Figure 13:
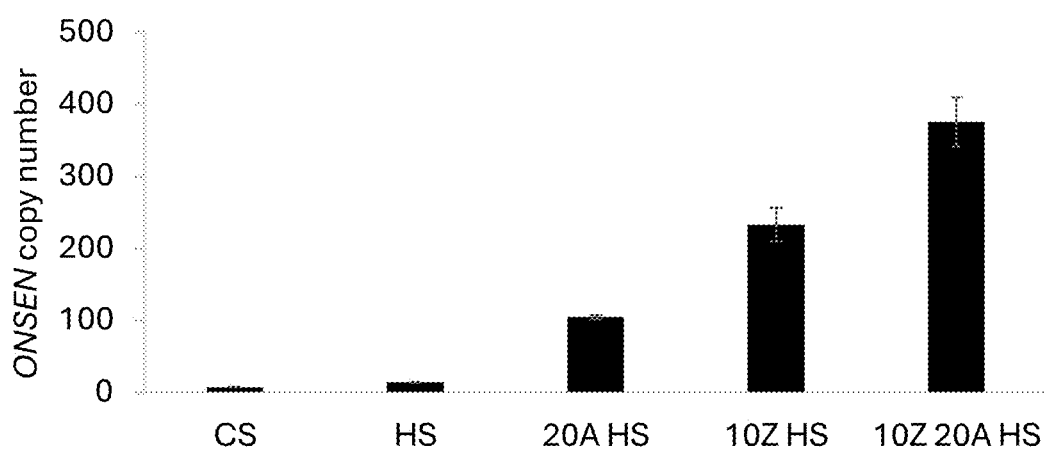

FIG. 13 shows accumulation of ONSEN extrachromosomal DNA upon pharmacological treatment and heat stress. ONSEN copy number was measured by quantitative PCR (qPCR) on total DNA in seedlings of WT directly after control stress (CS; 24 h 6° C.), heat stress (HS; 24 h 6° C. and 24 h 37° C.) and HS plus treatment with alpha-aminitin (A, 20 µg/ml), zebularine (Z, 10 µM) and HS plus the combination of A&Z. This result demonstrates the robustness of the treatments independent of the relative concentrations of A and Z.

EXAMPLES

The inventors have discovered a highly efficient method to activate and mobilize TEs in eukaryotes. The treatment involves drugs that target highly conserved eukaryotic mechanisms: DNA methylation and transcription.

Example 1

Figure 3C:
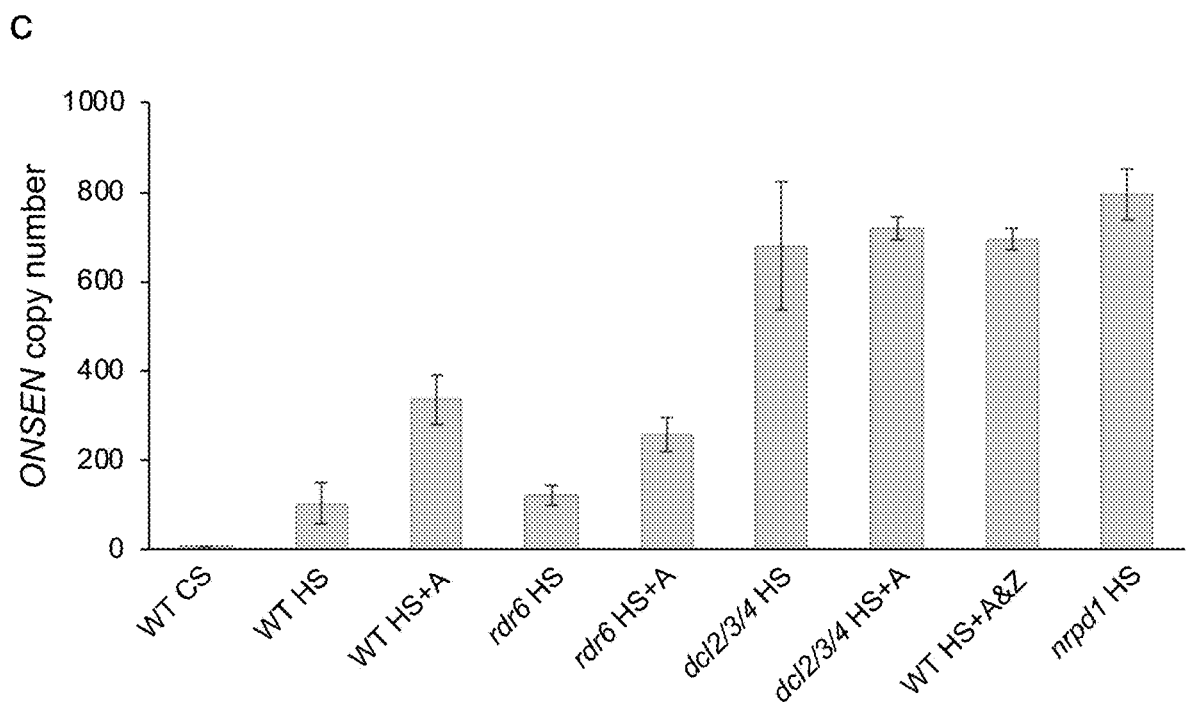

In order to investigate the role of Pol II on TE mobility the inventors chose the well-characterized heat-responsive copia-like ONSEN retrotransposon (Ito, H. et al., Nature, 2011, 472: 115-119) of *Arabidopsis*. The inventors first tested if Pol II deficient plants showed enhanced TE activity. For that purpose, the inventors took advantage of the hypomorphic nrpb2-3 mutant allele that accumulates reduced NRPB2 protein levels (Zeng, B. et al., Genes Dev, 2009, 23: 2850-2860). Using real-time PCR, it was determined that challenging nrpb2-3 seedlings by heat stress (called HS here) lead to a mild increase in ONSEN ecDNA compared to the wild type (FIG. 1a). This result was supported by the observed increase in ONSEN ecDNA after pharmacological inactivation of Pol II with 5 µg/ml α-amanitin (called A here), a potent Pol II inhibitor that does not affect Pol IV or Pol V (Haag, J. R. et al., Mol Cell, 2012, 48: 811-818) (FIG. 1a,b). Transcription by RNA Polymerase II (Pol II) is inhibited by α-amanitin, derivatives thereof or other Pol II inhibitors. Global inhibition of DNA methylation is achieved by treatments with zebularine or 5-aza-2'-deoxycytidine (and derivatives thereof). In order to test the interaction between Pol II-mediated repression of TE activation and DNA methylation the inventors grew wild-type and nrpb2-3 plants on media supplemented with moderate amounts of zebularine (called Z here, 40 µM for wild-type plants, 10 µM for nrpb2-3 plants to ensure the viability of nrpb2-3 seedlings), an inhibitor of DNA methyltransferases active in plants (Baubec, T. et al., Plant J, 2009, 57: 542-554) and submitted them to HS. The presence of Z in the medium during HS generally enhanced the production of ONSEN ecDNA. Notably, this induced increase in ecDNA accumulation was more distinct in the nrpb2-3-background (FIG. 1a). This indicated that both, DNA methylation and Pol II transcriptional activity contribute to the repression of ONSEN ecDNA production. Because both DNA methylation and Pol II can be specifically inhibited by the addition of different drugs the inventors tested if treating wild-type plants with both A and Z at the same time could strongly activate and even mobilize ONSEN after a heat stress treatment. The inventors grew WT seedlings on MS medium supplemented with each drug individually and both combined. In conformity with the strong activation of ONSEN in heat stressed and Z-treated nrpb2-3-seedlings, the combined treatment (A+Z) of the WT gave rise to a very high (FIG. 1b) and HS-dependent (FIG. 2) accumulation of ONSEN ecDNA comparable to the nrpd1 mutant (FIG. 3c).

Example 2

In order to better understand the effect the drugs had at the DNA level underlying the increased activation of ONSEN after HS, the inventors assessed how they influenced DNA methylation at the long terminal repeat (LTR) of a selected ONSEN endogenous locus (AT1TE12295) and at an unrelated well characterized RdDM target (soloLTR). Treating plants with A or Z individually already resulted in reduced CHH methylation levels at the ONSEN LTR after CS (FIG. 3a). Combining the two drugs lead to a loss of DNA methylation comparable to the nrpd1 mutant. DNA methylation at the soloLTR showed a different response to the drug treatments as a reduction in DNA methylation levels was only observed in plants submitted to a combined A and Z treatment. The inventors then checked by Northern Blot whether the degree of reduction in CHH methylation would coincide with increased ONSEN-transcript-levels directly after HS. The inventors found that treatment with Z alone already resulted in the highest ONSEN-transcript levels after HS (FIG. 3b). From this observation, the inventors concluded that these additional Z-induced transcripts were not suitable templates for the production of ONSEN ecDNA (compare FIG. 1 and FIG. 3b).

In *Drosophila*, it has been shown that Pol II-mediated antisense transcription results in the production of TE-derived siRNAs in a Dicer-2 dependent manner (Russo, J. et al. Genetics, 2016, 202:107-21). Supporting this notion for *Arabidopsis*, a recent publication pointed out the importance of DCL3 in regulating ONSEN in the ddm1 background (Panda, K. et al. Genome Biol, 2016, 17:1-19). To elucidate whether the effect of Pol II inhibition was also dicer-dependent, the inventors grew both the rdr6- and the dcl2/3/4-triple mutant (defective in three of the four plant dicer-like enzymes, DCLs) on A, applied HS and measured ONSEN ecDNA. The inventors found that A was still enhancing ecDNA accumulation in rdr6 whereas inhibition of Pol II had no effect in the dcl2/3/4 triple-mutant (FIG. 3c). This finding supports the notion that Pol II acts upstream of the processing step catalyzed by the DCLs.

Example 3

Figure 4A:
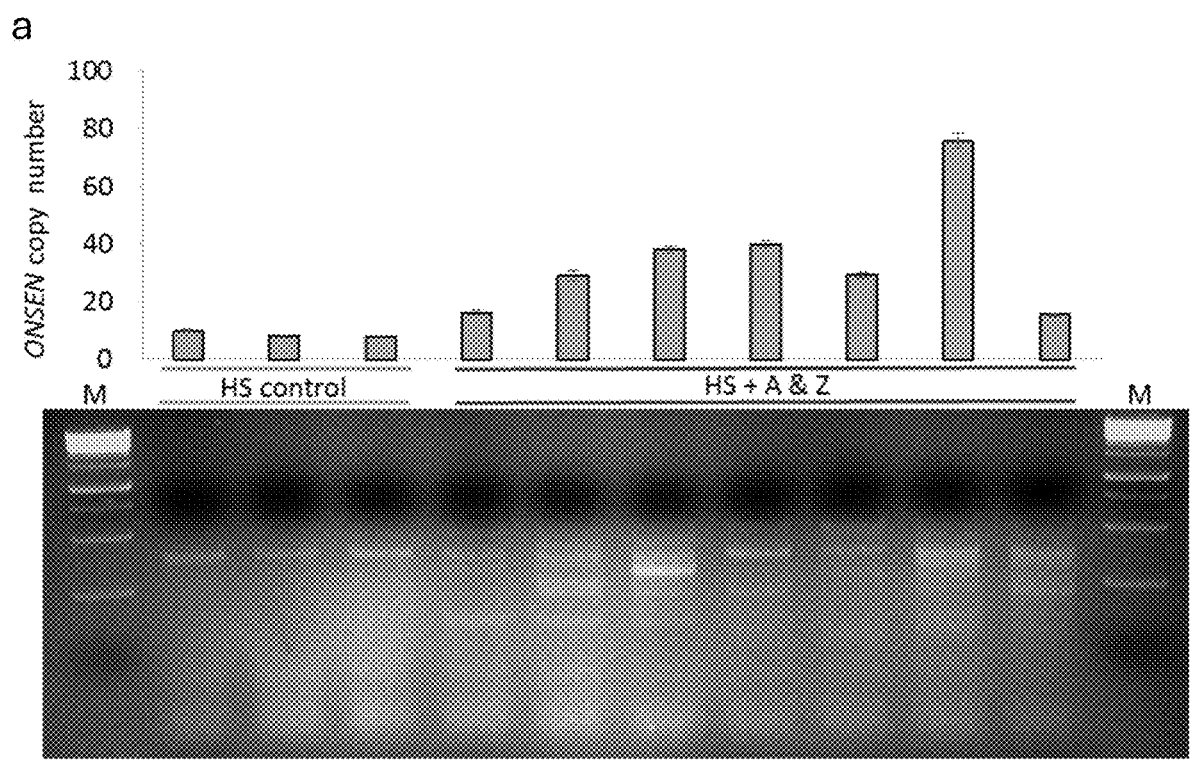
Figure 4B:
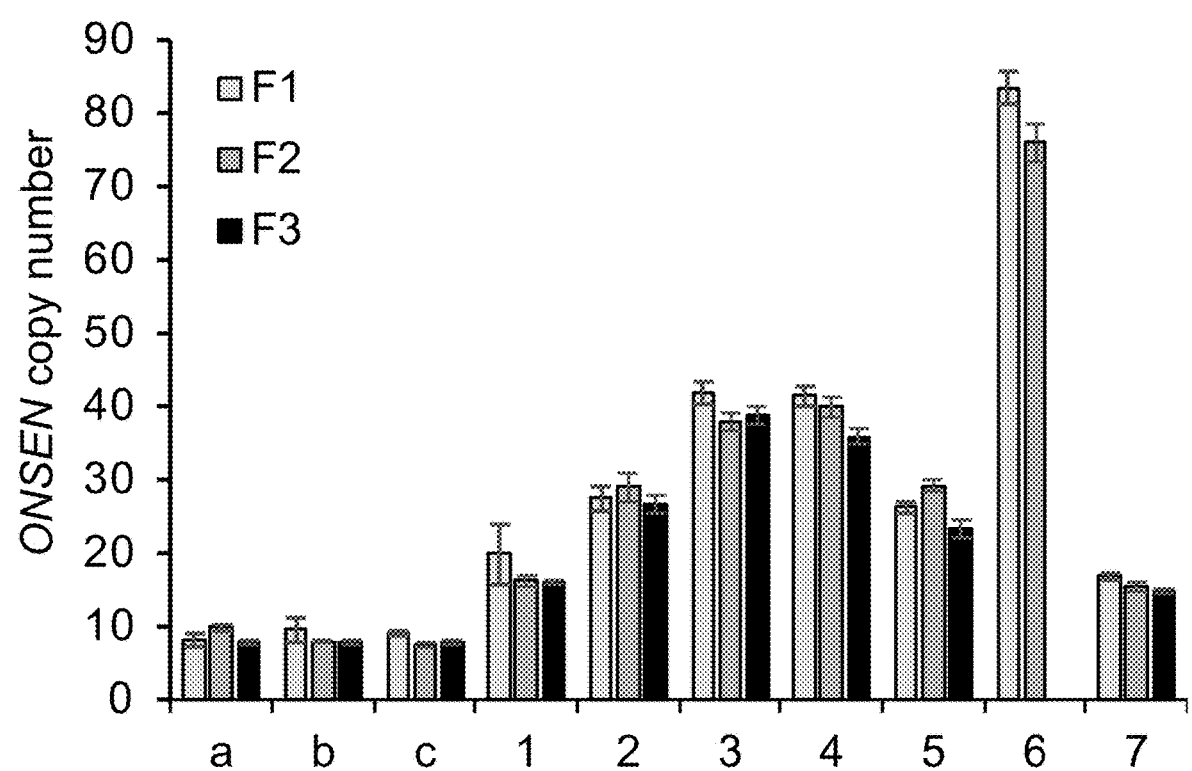

Mobilization of endogenous TEs in plants has so far been very inefficient, thus limiting their use in basic research and plant breeding. We have previously not observed ONSEN transposition in HS treated wild-type plants (Ito, H. et al. Nature, 2011, 472:115-119). Because the A&Z drug treatment resulted in an increased ONSEN ecDNA accumulation to a similar degree like in nrpd1, the inventors tested if the combined drug treatment could lead to an efficient ONSEN mobilization in wild-type plants. First, the inventors assessed by real-time PCR if, and at which frequencies, new ONSEN copies could be detected in the progeny of A&Z-treated and heat stressed plants. The inventors found new ONSEN insertions in 29.4% of the tested F1 pools (n=51) with mean copy numbers of the pools reaching up to 52 (FIG. 5). The inventors then confirmed stable novel ONSEN insertions in a subset of independent individual high copy plants by transposon display (FIG. 4a), real-time PCR (FIG. 4b) and sequencing of some insertions in a selected high-copy line (#3) (FIG. 6). The combination of HS, A and Z resulted in a similar extrachromosomal ONSEN copy number as has been previously observed in RdDM deficient plants. The inventors detected novel ONSEN insertions in the progeny of 27% of the treated plants. According to qPCR measurements, up to 90+/−6 inserted copies were detected in individual plants in the F2 and successive generations of A, Z and HS treated plants (FIG. 4a). These insertions were further confirmed by transposon display. The inventors did not observe further increases in ONSEN copy numbers over three generations indicating that the new insertions were stable and that ONSEN was not transposing anymore (FIG. 4b).

TE insertions can interrupt genes or alter their expression by either recruiting epigenetic marks or by stress-dependent readout transcription from the 3'LTR into flanking regions (Lisch, D., Nat Rev Genet, 2013, 14: 49-61). To test this, the inventors grew the F2 generation of the aforementioned selected high copy lines under long and short day conditions. The inventors observed that many lines showed clear and homogenous phenotypes in response to the different growth conditions (plant size, chlorophyll content and flowering time, FIGS. 4c and d).

Example 4

Figure 7A:
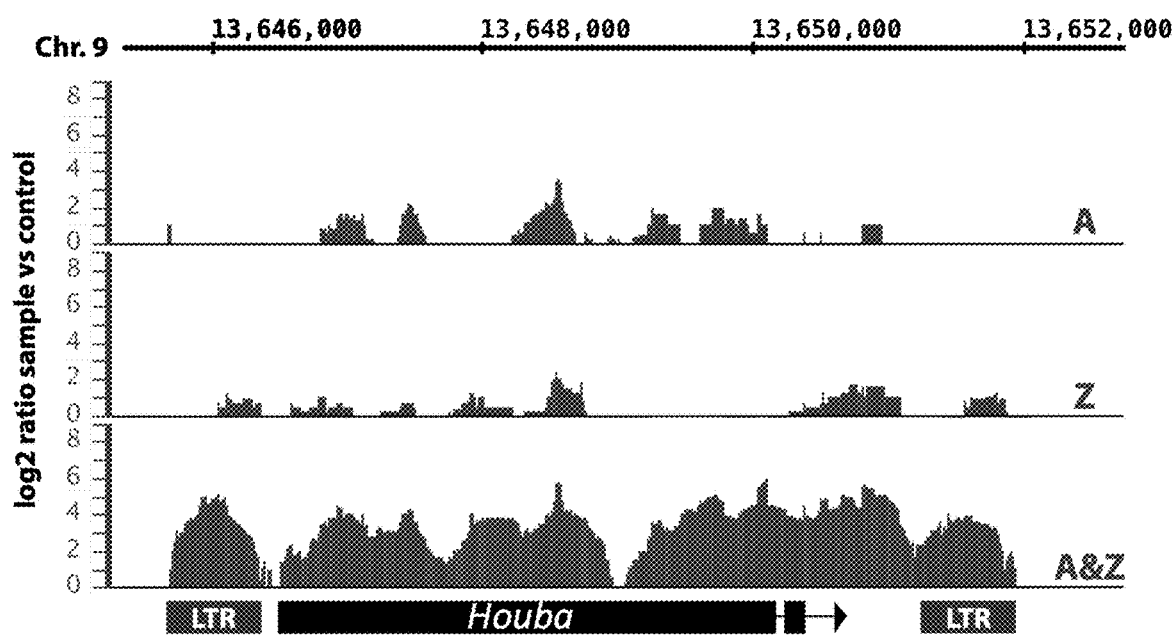

The inventors tested if Pol II plays a more general role in repressing TEs in plants. Due to its significantly different epigenetic landscape compared to Arabidopsis the inventors chose the genetically well characterized monocotyledonous rice crop O. sativa (Kawahara, Y. et al., 2013, Rice, 6: 4-10). In order to capture drug-induced mobilized TEs, the inventors characterized the active mobilome in O. sativa seedlings that were grown on MS medium supplemented either with no drugs, A only, Z only or the combination of A and Z, using a method that allows to specifically sequence extrachromosomal circular DNA (eccDNA). eccDNA is a byproduct of the LTR retrotransposon life cycle. Using this approach, the inventors identified Houba, a copia like retrotransposon (Panaud, O. et al., Mol. Genet. Genomics, 2002, 268:113-121), as highly activated only when plants were treated with both A and Z (FIG. 7a). The sequencing data were confirmed by an eccDNA-specific PCR on the Houba LTRs (FIGS. 7b and c).

Example 5

Because the treatment with A alone reduced DNA methylation (FIG. 3a) in Arabidopsis, the inventors wanted to test the robustness and generality of this treatment. In order to confirm the robustness, plants were treated with A (20 µg/ml), Z (10 µg/ml) and A&Z. A alone already strongly reduced DNA methylation at this higher concentration (FIG. 10a), this result was then further supported by the assessment of DNA methylation in the CHH context by bisulfite sequencing (average of 10 sequenced clones for each sample). Because A inhibits the highly conserved RNA Pol II enzyme and that A is also active in human cells, the inventors tested the effect of A on DNA methylation in the A549 human cancer cell line. Global DNA methylation content in the cells was assessed and compared to untreated or Z-treated cells. Supplementation of the growth medium with A (0.5 µg/ml) resulted in a 40% reduction of DNA methylation. This reduction was comparable to a treatment with the DNA demethylating agent Z (350 µM) (FIG. 10c). The authors then also assessed the DNA methylation levels at the long interspersed element 1 (LINE-1) retrotransposon. At LINE-1 A had an even more pronounced effect on the reduction of DNA methylation than Z (40% versus 20% reduction, respectively). These results demonstrate that an inhibitor of transcription can be used as a potent DNA demethylating agent in eukaryotic cells.

Plants and Growth Conditions

After stratification for two days at 4° C., Arabidopsis thaliana plants (accession Col-0) were grown on sterile ½ MS medium with 1% sucrose and a pH of 5.8 (control medium) under long day conditions (16 h light) at 24° C. (day) and 22° C. (night), respectively. Oryza sativa plants were grown on sterile ½ MS medium with 1% sucrose and a pH of 5.8 (control medium) 16 h at 28° C. (day) and 27° C. (night), respectively.

In order to analyze successive generations, seedlings were transferred to soil and grown under long day conditions (16 h light) at 24° C. (day) and 22° C. (night) (A. thaliana) in a Sanyo MLR-350 growth chamber until seed maturity.

For phenotyping, A. thaliana plants were grown under long day conditions (16 h light) at 24° C. (day) and 22° C. (night) and short day conditions (10 h light) at 21° C. (day) and 18° C. (night).

The induction of epigenetic changes and the activation and stable integration of transposable elements in Arabidopsis seedlings was enhanced by germinating and growing them on ½ MS-medium that contained zebularine (final concentration: 10-40 µM), α-amanitin (final concentration: 0.005-20 µg/ml) or a combination of both chemicals (inductive media).

In order to trigger the transposition of the heat-responsive retrotransposon ONSEN, seven days old seedlings were exposed to a cold shock for 24 h at 6° C. followed by a heat-stress for 24 h at 37° C. (heat stress, HS) under controlled conditions in a growth chamber (Sanyo). Control plants were transferred back to longday-conditions 24° C. (day) and 22° C. (night) after the cold treatment at 6° C. for 24 h (CS, control stress, according to Ito et al., 2011).

In order to trigger a biotic-stress response, nine days old *Arabidopsis*-seedlings were grown for nine days on 5 ug/ul alpha-amanitin and 40 uM zebularine and sprayed with flg22 (10 μM). After 5 h of incubation, total DNA from the aerial part of seedlings was extracted and TE copy number assessed by qPCR.

qPCRs on Total DNA to Measure ONSEN and COP/A17 Copy Numbers

Total DNA from seedlings and adult plants was isolated using a DNeasy Plant Mini Kit (QIAGEN).

In preparation to the measurement of extrachromosomal DNA copies of ONSEN in CS/HS and untreated/treated seedlings, roots were dissected directly after the heat stress and plants were immediately frozen in liquid nitrogen until DNA extraction.

To track ONSEN copy numbers in the F1-F3 generations of control and high copy lines, DNA from true leaves was extracted.

For the estimation of the ONSEN transposition frequency, total DNA of pools consisting of at least eight seedlings of the progeny of HS+A&Z-treated plants was isolated. The DNA concentration was measured with a Qubit Fluorometer (Thermo Fisher Scientific).

The copy numbers of ONSEN were determined with qPCRs on total DNA using a TaqMan master mix (Life Technologies) in a final volume of 10 μl in the Light-Cycler 480 (Roche). ACTOPIA17 copy number was measured by quantitative PCR (qPCR) in a Light-Cycler 480 (Roche), using XYBR 421 Green I Master Mix. Actin2 (At3g18780) served as a standard gene for normalization. The sequences of the primers and probes for the qPCRs are listed in table 2.

For the mobilome-seq analysis DNA from the aerial parts of three *O. sativa* seedlings was extracted as previously reported (Mette, M. et al., EMBOJ, 1999, 18: 241-248).

5 μg of genomic DNA for each sample were purified using a Geneclean kit (MPBio, USA) according to the manufacturer's instructions. ecDNA was isolated from the GeneClean product using the PlasmidSafe DNase (Epicentre, USA) according to the manufacturer's instructions, except that the 37° C. incubation was performed for 17 h. DNA samples were precipitated by adding 0.1 volume of 3M sodium acetate (pH 5.2), 2.5 volumes of ethanol and 1 ul of glycogen (Fisher, USA) and incubating overnight at −20° C. The precipitated circular DNA was amplified by random rolling circle amplification using the Illustra TempliPhi kit (GE Healthcare, USA) according to the manufacturer's instructions except that the incubation was performed for 65 h at 28° C. The DNA concentration was determined using the DNA PicoGreen kit (Invitrogen, USA) using a LightCycler480 (Roche, USA). One nanogram of amplified ecDNA from each sample was used to prepare the libraries using the Nextera XT library kit (Illumina, USA) according to the manufacturer's instructions. DNA quality and concentration were determined using a high sensitivity DNA Bioanalyzer chip (Agilent Technologies, USA). Samples were pooled and loaded onto a MiSeq platform (Illumina, USA) and 2×250 nucleotides paired-end sequencing was performed. Quality control of FASTQ files was evaluated using the FastQC tool (version 0.10.1). To remove any read originating from organelle circular genomes, reads were mapped 198 against the mitochondria and chloroplast genomes using the program Bowtie2 version 2.2.2 71 with—sensitive local mapping. Unmapped reads were mapped against the reference genome IRGSP1.0 (http://rgp.dna.affrc.go.jp/E/IRGSP/Build5.html) using the following parameters:—sensitive local, -k 1. DNA from both mitochondria and chloroplast genomes integrated in nuclear genomes was masked (1,697,400 bp), The TE containing regions cover 194,224,800 bp in *O. sativa*. Finally, for each library, a .bam alignment file corresponding to enriched genomic regions was considered for statistical analysis and visualized with the Integrative Genomics Viewer (IGV) software, available online at broadinstitute.org/igv/home.

TABLE 2

Sequences of primers and probes that were used for the qPCRs (TaqMan, Life Technologies) to measure total number of extrachromosomal ONSEN DNA-copies. Actin 2 served as a control gene for normalization.

| Primer | Sequence 5'→3' |
| --- | --- |
| SEQ ID No 001 (ONSEN_RT_fw) | CCACAAGAGGAACCAACGAA |
| SEQ ID No 002 (ONSEN_RT_rev) | TTCGATCATGGAAGACCGG |
| SEQ ID No 003 (ONSEN probe) | (FAM)AAGTCGGCAATAGCTTTGGCGAAGA(BHQ1) |
| SEQ ID No 004 (Actin2_RT_fw) | TGCCAATCTACGAGGGTTTC |
| SEQ ID No 005 (Actin2_RT_rev) | TTACAATTTCCCGCTCTGCT |
| SEQ ID No 006 (Actin2_probe) | (JOE)TCCGTCTTGACCTTGCTGGACG(BHQ-1) |
| SEQ ID No 007 (GenWalkAdaptator1) | GTAATACGACTCACTATAGGGCACGCGTGGTCGACGGCCCGGGCTGGT |
| GenWalkAdaptor2 | (PHOS)ACCAGCCC(AMINO) |

TABLE 2-continued

Sequences of primers and probes that were used for the qPCRs (TaqMan, Life Technologies) to measure total number of extrachromosomal ONSEN DNA-copies. Actin 2 served as a control gene for normalization.

| Primer | Sequence 5'→3' |
| --- | --- |
| SEQ ID No 008 (AP1) | GTAATACGACTCACTATAGGGC |
| SEQ ID No 009 (Copia78 3' LTR) | AACACTTAAACACTTTCTCCA |
| SEQ ID NO 010 706_ATCOPIA17 QT R | TTAGTATAAGGCTGAGCTGGAAACTG |
| SEQ ID NO 011 705_ATCOPIA17 QT F | CAAGCCTAACCCTCAGCTACATG |

Transposon Display to Confirm Insertion of New ONSEN Copies

The stable integration of additional copies of the ONSEN TE into the genome of heat stressed and treated plants was ascertained by a simplified transposon display based on the GenomeWalker Universal kit (Clontech Laboratories), according to Ito et al. 2011.

300 ng of total DNA from adult plants from the F2 generation of HS+/−A & Z was extracted with a DNeasy Plant Mini Kit (QIAGEN) and digested with a blunt cutter restriction enzyme (Dra I). After purification with a High Pure PCR Product Purification Kit (Roche) digested DNA was ligated to the annealed GenWalkAdapters 1 & 2. For the PCR, the adaptor specific Primer AP1 and the ONSEN-specific Primer Copia 78 3' LTR was used. The PCR products were separated on a 2% agarose gel that was stained with a Midori Green Nucleic Acid Staining Solution. For sequence information, see tables 2 and 3.

Cloning, Sequencing and Genotyping of New Insertions

In order to identify the genomic region of new ONSEN insertions, the PCR product of the transposon display was purified using a High Pure PCR Product Purification Kit (Roche), ligated into a pGEM-T Vector (Promega) and transformed into *E. coli*. After a blue white selection, positive clones were used for the insert amplification and sequencing (StarSEQ). The obtained sequences were analyzed with Geneious 8.2.1 and blasted against the *Arabidopsis thaliana* reference genome. The standard genotyping-PCRs to prove novel ONSEN insertions were performed with combinations of the ONSEN-specific primer "Copia 78 TE display 3'LTR" and primers listed in tables 2 and 3.

TABLE 3

Names, purpose and sequences of primers

| Name/SEQ ID NO | Sequences 5'→3' | Experiment |
| --- | --- | --- |
| OnsenFull_F SEQ ID 12 | AAGTGGTATCAGAGCTTGAAGATCC | Northern Blot |
| OnsenFull_R SEQ ID 13 | CAACACCCCTCTTAAACTTGATTTTGC | |
| M13F SEQ ID 14 | CGCCAGGGTTTTCCCAGTCACGAC | Cloning and |
| M13R SEQ ID 15 | TCACACAGGAAACAGCTATGAC | sequencing |
| 286 OnsenBis F1 SEQ ID 16 | GGTTGAAGGGTYAAAGAGTAAAT | Methylation analysis |
| 287 OnsenBis R1 SEQ ID 17 | CCTCCAAACTACAAAATATCTAAAA | |
| 835 Chop PCR ACT2 F SEQ ID 18 | TGTAGTGTCGTACGTTGAACAGAAAGC | |
| 836 Chop PCR ACT2 R SEQ ID 19 | TTGGCACAGTGTGAGACACACCA | |
| houba_F2 SEQ ID 20 | ATCCTGGGAAGAACAAACCATTAA | PCR on |
| houba_R2 SEQ ID 21 | GAGTTCGAGTACCTTAGCCATGGT | circular rice TE |
| Chloroplast cyc F SEQ ID 22 | ACAACCACTGATGAAGGATT | and chloroplast |
| Chloroplast cyc R SEQ ID 23 | AGAAAGAAAAGCAACGACTG | control |
| Prove TED 2_20 R SEQ ID 24 | ACCTAGCTCTGAGTGATGAA | Genotyping of novel ONSEN |
| Prove TED4_27 F SEQ ID 25 | TGGATATACACATTGGTTGCA | insertions |
| Prove TED 2_19 F SEQ ID 26 | GGAGAAAGCTGAAAACTTGG | |

TABLE 3-continued

Names, purpose and sequences of primers

| Name/SEQ ID NO | Sequences 5'→3' | Experiment |
|---|---|---|
| Prove TED4_30_rev SEQ ID 27 | CTAGGTTGGTGACTGATGAG | |
| Prove TED 2_17 F SEQ ID 28 | AAGAATGGGAGCAGCATTAA | |
| Prove3_2R SEQ ID 29 | GCAGTACTATAACCGGGACT | |
| prove TED3_1 Fw SEQ ID 30 | GAACTTTCCGTTGTTACCGG | |
| Prove TED3 F SEQ ID 31 | ATGAGACAGGGAGCTTATCT | |
| Prove TED1 R SEQ ID 32 | GGTGTGAACCGAACCTAAAT | |
| Prove TED 4_25 F SEQ ID 33 | AAACACCAGAAATCTTTCGC | |

PCRs on Extrachromosomal *Houba* DNA

The presence of circular *Houba*-copies was proven by an inverse PCR on 7 ng of the rolling-circle amplified template that was also used for sequencing. A PCR specific to a chloroplast DNA served as a loading control. PCR products were separated on a 1% agarose gel that was stained with a Midori Green Nucleic Acid Staining Solution (Nippon Genetics Europe). Primer sequences are given in supplementary Table 4.

TABLE 4

Sequences of primers and probes that were used for the PCRs to measure total number of extrachromosomal Houba DNA.

| Primer/SEQ ID NO | Sequence 5'→3' |
|---|---|
| 286 OnsenLTRchopF SEQ ID 34 | GGTTGAAGGGTYAAAGAGTAAAT |
| 287 OnsenLTRchopR SEQ ID 35 | CCTCCAAACTACAAAATATCTAAAA |
| Houba_F2 SEQ ID 36 | ATCCTGGGAAGAACAAACCATTAA |
| Houba_R2 SEQ ID 37 | GAGTTCGAGTACCTTAGCCATGGT |

RNA Analysis and Northern Blot

Total RNA from the aerial part of *Arabidopsis* seedlings was isolated using the TRI Reagent (Sigma) according to manufacturer's recommendations. RNA concentration was measured (Qubit RNA HS Assay Kit, Thermo Fisher), 15 µg of RNA was separated on a denaturing 1.5% Agarose gel, blotted on a Hybond-N+ (GE Healthcare) membrane and hybridized with 25 ng of a gel-purified and P32 labelled probe (Megaprime DNA Labelling System, GE Healthcare) specific to the full length ONSEN transcript (See table 3 for primer sequences).

DNA Methylation Analysis 20 ng of total genomic DNA isolated from *Arabidopsis* seedlings was digested with the methylation sensitive restriction enzyme, Dde1 (NEB) at 37° C. over night. Following heat inactivation at 60° C. for 20 min, the digested DNA was used as a template for the chopPCR. Actin2 served as a control for the digest. Undigested DNA was used as a loading control. PCR products were separated on a 1% agarose gel and stained with Midori Green.

For the A549 human cancer cell line cells were grown in medium without treatment or supplemented with either Z (350 µM) or A (0.5 µg/ml), DNA was extracted by using the QiaAmp DNA mini Kit (Qiagen, France). Next, global DNA methylation was estimated by quantifying the presence of 5-methylcytosine 5-mC DNA ELISA Kit (Zymo Research) according to the manufacturers's instructions. DNA methylation at the LINE-1 transposons were assessed with the Global DNA Methylation Assay—LINE-1 kit (Active Motif).

The invention claimed is:

1. A method for increasing resistance to an abiotic stress in a plant population by mobilizing transposable elements in a plant cell comprising:
   providing plant cells,
   contacting said plant cells with
      an inhibitor of DNA methylation, wherein the inhibitor of DNA methylation is zebularine, and
      an inhibitor of RNA Polymerase II, wherein the inhibitor of RNA Polymerase II is alpha-amanitin,
   exposing said plant cells to an abiotic stress,
   propagating plants from said plant cells while exposing said plants to the abiotic stress, and
   selecting those propagated plants with increased resistance to the abiotic stress in comparison to plants propagated from cells that were not contacted with the inhibitor of DNA methylation and the inhibitor of RNA Polymerase II, and
   wherein the plant cells are wheat plant cells and the abiotic stress is cold or salinity;
   wherein the plant cells are rice plant cells and the abiotic stress is heat or drought; or
   wherein the plant cells are *Arabidopsis* plant cells and the abiotic stress is heat.

2. The method according to claim 1, further comprising:
   a. determining any genetic changes in said plants, and/or
   b. determining any changes in the phenotype of said plants in addition to the increased resistance to the abiotic stress,
   wherein said genetic or phenotypical changes are determined in the individual plants or for a representative sample of the plant, or for all of the constituent plants of the plant population.

3. The method according to claim 1, wherein said alpha-amanitin is used at a concentration of 0.0005 µg/ml to 50 µg/ml.

4. The method according to claim 1, wherein said zebularine is used at a concentration of 5 µM to 100 µM.

* * * * *